United States Patent
Das et al.

(10) Patent No.: US 7,371,825 B2
(45) Date of Patent: May 13, 2008

(54) ANTI-MCP-1 ANTIBODIES, COMPOSITIONS, METHODS AND USES

(75) Inventors: Anuk Das, Wayne, PA (US); Jill M. Carton, Malvern, PA (US)

(73) Assignee: Centocor, Inc., Malvern, PA (US)

( * ) Notice: Subject to any disclaimer, the term of this patent is extended or adjusted under 35 U.S.C. 154(b) by 0 days.

(21) Appl. No.: 11/170,453

(22) Filed: Jun. 29, 2005

(65) Prior Publication Data

US 2006/0039913 A1   Feb. 23, 2006

Related U.S. Application Data

(60) Provisional application No. 60/584,365, filed on Jun. 30, 2004.

(51) Int. Cl.
  *C07K 16/00* (2006.01)
  *C12P 21/08* (2006.01)
  *C07K 1/00* (2006.01)

(52) U.S. Cl. ................. 530/387.1; 530/387.3; 530/388.1; 530/388.23

(58) Field of Classification Search .................. None
See application file for complete search history.

(56) References Cited

OTHER PUBLICATIONS

Rudikoff et al. PNAS 1982 vol. 79, pp. 1979-1983.*
Rader et al. PNAS. 1998. 95:8910-8915.*
Eardley, K.S. et al 'The Relationship Between Albuminuria, MCP-1/CCL2, and Interstitial Macrophages in Chronic Kidney Disease' Kidney International (2006) vol. 69, pp. 1189-1197.
International Search Report re: PCT/US06/23025 dated Sep. 27, 2006.

* cited by examiner

*Primary Examiner*—Maher M. Haddad
*Assistant Examiner*—Chun Crowder

(57) ABSTRACT

The present invention relates to at least one novel anti-MCP-1 antibodies, including isolated nucleic acids that encode at least one anti-MCP-1 antibody, MCP-1, vectors, host cells, transgenic animals or plants, and methods of making and using thereof, including therapeutic compositions, methods and devices.

11 Claims, 5 Drawing Sheets

| | Specific bound cpm |
|---|---|
| One site binding (hyperbola) Best-fit values | |
| BMAX | 15656 |
| KD | 8.964 |

SEQUENCE LISTING

<160> NUMBER OF SEQ ID NOS: 17

<210> SEQ ID NO 1
<211> LENGTH: 5

```
<212> TYPE: PRT
<213> ORGANISM: Mus sp.

<400> SEQUENCE: 1

Asp Tyr Tyr Ile Asn
1               5

<210> SEQ ID NO 2
<211> LENGTH: 17
<212> TYPE: PRT
<213> ORGANISM: Mus sp.

<400> SEQUENCE: 2

Arg Ile Tyr Pro Gly Thr Gly Asn Thr Tyr Tyr Asn Glu Asn Phe Lys
1               5                   10                  15

Gly

<210> SEQ ID NO 3
<211> LENGTH: 14
<212> TYPE: PRT
<213> ORGANISM: Mus sp.

<400> SEQUENCE: 3

Ser Gly Ser Thr Val Val Gly Asn Tyr Tyr Gly Met Asp Tyr
1               5                   10

<210> SEQ ID NO 4
<211> LENGTH: 11
<212> TYPE: PRT
<213> ORGANISM: Mus sp.

<400> SEQUENCE: 4

Lys Ala Ser Gln Ser Val Ser Asn Asp Val Ala
1               5                   10

<210> SEQ ID NO 5
<211> LENGTH: 7
<212> TYPE: PRT
<213> ORGANISM: Mus sp.

<400> SEQUENCE: 5

Tyr Ala Ser Asn Arg Tyr Thr
1               5

<210> SEQ ID NO 6
<211> LENGTH: 9
<212> TYPE: PRT
<213> ORGANISM: Mus sp.

<400> SEQUENCE: 6

Gln Gln Asp Tyr Ser Ser Pro Trp Thr
1               5

<210> SEQ ID NO 7
<211> LENGTH: 142
<212> TYPE: PRT
<213> ORGANISM: Mus sp.

<400> SEQUENCE: 7

Met Gly Trp Ser Trp Ile Phe Phe Phe Leu Leu Ser Gly Thr Ala Gly
1               5                   10                  15

Val His Cys Gln Val Gln Leu Lys Gln Ser Gly Ala Glu Leu Val Arg
            20                  25                  30
```

```
Pro Gly Ala Ser Val Lys Leu Ser Cys Lys Ala Ser Gly Tyr Thr Phe
        35                  40                  45

Thr Asp Tyr Tyr Ile Asn Trp Val Lys Gln Arg Pro Gly Gln Gly Leu
    50                  55                  60

Glu Trp Ile Ala Arg Ile Tyr Pro Gly Thr Gly Asn Thr Tyr Tyr Asn
65                  70                  75                  80

Glu Asn Phe Lys Gly Lys Ala Thr Leu Thr Ala Glu Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Ser Gly Ser Thr Val Val Gly Asn Tyr Tyr Gly
        115                 120                 125

Met Asp Tyr Trp Gly Gln Gly Thr Ser Val Thr Val Ser Ser
        130                 135                 140
```

<210> SEQ ID NO 8
<211> LENGTH: 128
<212> TYPE: PRT
<213> ORGANISM: Mus sp.

<400> SEQUENCE: 8

```
Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Ser Ile Thr Cys Lys Ala Ser Gln Ser
        35                  40                  45

Val Ser Asn Asp Val Ala Trp Tyr Gln Gln Lys Pro Gly Gln Ser Pro
    50                  55                  60

Lys Leu Leu Ile Tyr Tyr Ala Ser Asn Arg Tyr Thr Gly Val Pro Asp
65                  70                  75                  80

Arg Phe Thr Gly Ser Gly Tyr Gly Thr Asp Phe Thr Phe Thr Ile Ser
                85                  90                  95

Thr Val Gln Ala Glu Asp Leu Ala Val Tyr Phe Cys Gln Gln Asp Tyr
            100                 105                 110

Ser Ser Pro Trp Thr Phe Gly Gly Gly Thr Lys Leu Glu Ile Lys Arg
        115                 120                 125
```

<210> SEQ ID NO 9
<211> LENGTH: 76
<212> TYPE: PRT
<213> ORGANISM: Homo sapiens

<400> SEQUENCE: 9

```
Gln Pro Asp Ala Ile Asn Ala Pro Val Thr Cys Cys Tyr Asn Phe Thr
1               5                   10                  15

Asn Arg Lys Ile Ser Val Gln Arg Leu Ala Ser Tyr Arg Arg Ile Thr
            20                  25                  30

Ser Ser Lys Cys Pro Lys Glu Ala Val Ile Phe Lys Thr Ile Val Ala
        35                  40                  45

Lys Glu Ile Cys Ala Asp Pro Lys Gln Lys Trp Val Gln Asp Ser Met
    50                  55                  60

Asp His Leu Asp Lys Gln Thr Gln Thr Pro Lys Thr
65                  70                  75
```

<210> SEQ ID NO 10
<211> LENGTH: 426

```
<212> TYPE: DNA
<213> ORGANISM: Mus sp.

<400> SEQUENCE: 10
atgggatgga gctggatctt tttcttcctc ctgtcaggaa ctgcaggtgt ccactgtcag      60
gtccagctga agcagtctgg ggctgagctg gtgaggcctg ggcttcagt gaaactgtcc     120
tgcaaggctt ctggctacac tttcactgac tactatataa actgggtgaa gcagaggcct    180
gggcagggac ttgagtggat tgcaaggatt tatcctggaa ctggtaatac ttactacaat    240
gagaatttca aggcaaggc cacactgact gcagaaaaat cctccagcac tgcctacatg     300
cagctcagca gcctgacatc tgaggactct gctgtctatt tctgtgcaag atcggggagt    360
acggtagtag ggaactacta tggtatggac tactggggtc aaggaacctc agtcaccgtc    420
tcctca                                                               426

<210> SEQ ID NO 11
<211> LENGTH: 384
<212> TYPE: DNA
<213> ORGANISM: Mus sp.

<400> SEQUENCE: 11
atgaagtcac agacccaggt cttcgtattt ctactgctct gtgtgtctgg tgctcatggg     60
agtattgtga tgacccagac tcccaaattc ctgcttgtat cagcaggaga cagggtttcc    120
ataacctgca aggccagtca gagtgtgagt aatgatgtag cttggtacca acagaagcca    180
gggcagtctc ctaaactgct gatatactat gcatccaatc gctacactgg agtccctgat    240
cgcttcactg gcagtggata tgggacggat ttcactttca ccatcagcac tgtgcaggct    300
gaagacctgg cagtttattt ctgtcagcag gattatagct ctccgtggac gttcggtgga    360
ggcaccaagc tggaaatcaa acgg                                           384

<210> SEQ ID NO 12
<211> LENGTH: 15
<212> TYPE: DNA
<213> ORGANISM: Mus sp.

<400> SEQUENCE: 12
gactactata taaac                                                      15

<210> SEQ ID NO 13
<211> LENGTH: 51
<212> TYPE: DNA
<213> ORGANISM: Mus sp.

<400> SEQUENCE: 13
aggatttatc ctggaactgg taatacttac tacaatgaga atttcaaggg c               51

<210> SEQ ID NO 14
<211> LENGTH: 42
<212> TYPE: DNA
<213> ORGANISM: Mus sp

<400> SEQUENCE: 14
tcggggagta cggtagtagg gaactactat ggtatggact ac                        42

<210> SEQ ID NO 15
<211> LENGTH: 33
<212> TYPE: DNA
<213> ORGANISM: Mus sp.
```

```
<400> SEQUENCE: 15
aaggccagtc agagtgtgag taatgatgta gct                           33

<210> SEQ ID NO 16
<211> LENGTH: 21
<212> TYPE: DNA
<213> ORGANISM: Mus sp.

<400> SEQUENCE: 16
tatgcatcca atcgctacac t                                        21

<210> SEQ ID NO 17
<211> LENGTH: 27
<212> TYPE: DNA
<213> ORGANISM: Mus sp.

<400> SEQUENCE: 17
cagcaggatt atagctctcc gtggacg                                  27
```

ANTI-MCP-1 ANTIBODIES, COMPOSITIONS, METHODS AND USES

The present application claims the benefit of priority to U.S. Provisional Application Ser. No. 60/584,365, filed Jun. 30, 2004, the contents of which are completely incorporated by reference. The application submitted herewith contains a Sequence Listing on computer readable disk which material is hereby incorporated by reference.

FIELD OF THE INVENTION

The present invention relates to antibodies which bind to the MCP-1, including specified portions or variants thereof. The antibodies of the invention are specific for at least one MCP-1 protein or fragment thereof. The invention also relates to nucleic acids encoding such anti-MCP-1 antibodies, complementary nucleic acids, vectors, host cells, and methods of making and using thereof, including therapeutic formulations, administration and devices.

BACKGROUND OF THE INVENTION

Monocyte chemoattractant protein 1 (MCP-1) belongs to the family of chemotactic cytokines known as chemokines. MCP-1 is expressed by a variety of cell types including monocytes, vascular endothelial cells, smooth muscle cells, glomerular mesangial cell, osteoblastic cells, and human pulmonary type-2-like epithelial cells (Sanders, S K. et al. *Journal of Immunology,* 165: 4877-4883, 2000). It is believed that MCP-1 plays an active role in the initiation and progression of inflammatory diseases, by promoting monocyte influx and subsequent activation in tissues. MCP-1 is chemotactic for monocytes but not neutrophils. It can induce the proliferation and activation of killer cells known as CHAK (CC—chemokine activated killer), which are similar to cells activated by IL-2. It regulates the expression of cell surface antigens (CD11c, CD11b) and the expression of cytokines (IL1, IL6). MCP-1 is a potent activator of human basophils, inducing the degranulation and the release of histamines.

MCP-1 is synthesized in human articular chondrocytes in response to a variety of inflammatory cytokines, and thus may play an active role in the initiation and progression of degenerative and inflammatory arthropathies by promoting monocyte influx and activation in synovial joints. Moreover, elevated levels of MCP-1 are observed in macrophage-rich atherosclerotic plaques. The factor activates the tumoricidal activity of monocytes and macrophages in vivo (www.copewithcytokines.de).

MCP-1 is known to bind and signal through the chemokine receptor, CCR2 (also known as RANTES). CCR2 is a seven trans-membrane-spanning G-protein-coupled receptor expressed on many cells including monocytes, T-cells, B-cells, and basophils. Two MCP-1 specific receptors, CCR2A and CCR2B, have been cloned which signal in response to nanomolar (nM) concentrations of MCP-1

MCP-1 is clearly involved in inflammatory and oxidative stress responses in the vasculature (See Kunsch, C., et al. Circ. 1999 Res. 85: 753-766). MCP-1 appears to play a role in angiogenesis, the formation of new blood vessels. Tumor cell-secreted MCP-1 levels correlate with blood vessel density in a number of tumors, including breast cancer (Saji, H., et al. Cancer, 92: 1085-1091, 2001; Ueno, T., et al. Clin Cancer Res, 6: 3282-3289, 2000), squamous cell carcinoma of head and neck (Liss, C., et al. Int J Cancer, 93: 781-785, 2001) and esophagus (Ohta, M., et al. Int J Cancer, 102: 220-224, 2002), gastric carcinoma (Ohta, M., et al. Int J Oncol, 22: 773-778, 2003), and hemangioma (Isik, F. F., et al. J Surg Res, 61: 71-76, 1996). Furthermore, high levels of tumor MCP-1 were also found to serve as a prognostic biomarker indicating poor prognosis and early relapse (Ueno, et al., 2000 supra; Liss, C., et al. Int J Cancer, 93: 781-785, 2001). It has been postulated that MCP-1 in tumor tissues may stimulate angiogenesis by recruiting tumor infiltrating macrophages and subsequent production of angiogenenic growth factors such as vascular endothelial growth factor, tumor necrosis factor $\alpha$, and interleukins 6 and 8 (Ueno, T., et al. 2000 supra; Liss, C., et al. 2001, supra). However the precise mechanisms underlying the role of MCP-1 in tumor angiogenesis have yet to be determined.

Other proteins with certain functional and sequence homology to human MCP-1 are known. Especially similar to MCP-1 (GenBank NP_002973) are MCP-2 (GenBank NP_005614) and eotaxin (GenBank P_51671); MCP-2 having 61.8 percent and eotaxin-1 having 63.2 percent sequence identity to MCP-1. The range of activities and spectrum of involvement of these proteins in human homeostatic mechanisms and pathology is not as well understood for the homologs of MCP-1. For example, MCP-2 is related closely to MCP-1 and MCP-3 (Genbank NP_006264) and uses both CCR1 as well as CCR2B as its functional receptors. MCP-3 binds to a receptor designated D6. MCP-3 also binds to CCR10. The MCP-3 protein (97 amino acids) sequence shows 74 percent identity with MCP-1 and 58 percent homology with MCP-2. Secreted MCP-3 differs from MCP-1 in being N-glycosylated. MCP-4 (Genbank NP_005399) shares 56-61 percent sequence identity with the three known monocyte chemotactic proteins and is 60 percent identical with Eotaxin-1. The functions of MCP-4 appear to be highly similar to those of MCP-3 and Eotaxin. Like MCP-3, MCP-4 is a potent chemoattractant for monocytes and T-lymphocytes. It is inactive on neutrophils. On monocytes MCP-4 binds to receptors that recognize MCP-1, MCP-3, and RANTES (CCR2). On eosinophils MCP-4 has similar efficacy and potency as MCP-3, RANTES, and Eotaxin. MCP-4 shares receptors with eotaxin (CCR1 and CCR3) and shows full cross-desensitization with eotaxin-1.

Other antibodies capable of binding MCP-1 have been reported: JP9067399 discloses an antibody obtained from isolated blood cells and JP05276986 discloses a hybridoma secreting an IgM anti-human MCP-1. More recently, antibodies capable of binding a plurality of beta-chemokines including MCP-1 were disclosed (WO03048083) and an MCP-1 binding antibody which also binds eotaxin (US20040047860).

Accordingly, there is a need to provide human antibodies specific for human MCP-1 for use in therapy to diminish or eliminate symptoms of MCP-1-dependent diseases, as well as improvements over known antibodies or fragments thereof.

SUMMARY OF THE INVENTION

The present invention provides isolated anti-human MCP-1 antibodies, immunoglobulins, cleavage products and other specified portions and variants thereof, as well as anti-MCP-1 antibody compositions, encoding or complementary nucleic acids, vectors, host cells, compositions, formulations, devices, transgenic animals, transgenic plants, and methods of making and using thereof, as described and enabled herein, in combination with what is known in the art. The antibodies of the invention bind MCP-1 with particular affinity and specificity, which binding is highly specific for human MCP-1 and not specific for other homologous polypeptides such as MCP-2, MCP3, MCP-4 or eotaxin. Accordingly, the antibodies can be used in a variety of methods for diagnosing, treating, and/or preventing diseases involving or mediated by activation of the MCP-1 receptor, particularly diseases involving MCP-1 mediated angiogenesis, such as prostate cancer, colon cancer, and renal carcinoma.

Thus, in one embodiment, the present invention provides at least one isolated anti-MCP-1 antibody as described herein. In one embodiment, the antibody according to the present invention includes any protein or polypeptide that comprises at least a portion of an ligand binding region of a heavy or light chain variable domain derived from the antibody designated C775, optionally in combination with a heavy chain or light chain variable region, a heavy chain or light chain constant region, a framework region, or any portion thereof, that can be incorporated into an antibody of the present invention, such as a Fab, F(ab')2, Fv, or a single chain Fv fragment. The antibody C775 described herein is a murine anti-human MCP-1 antibody derived from immunization of a Balb/c mouse with DNA encoding the human MCP-1 polypeptide. Particular therapeutic antibodies of the invention include monoclonal antibody C775, and functionally equivalent antibodies which have the heavy chain or light chain binding domain amino acid sequences in their variable regions as set forth in SEQ ID NO: 7 and SEQ ID NO: 8 respectively, and conservative modifications thereof.

Still other particular antibodies of the invention include those which comprise the CDR1, CDR2, and CDR3 of the murine heavy chain regions selected from the group consisting of the amino acid sequences of the CDR1, CDR2, and CDR3 regions shown in SEQ ID NOs: 1, 2 and 3, and conservative sequence modifications thereof, and (b) the CDR1, CDR2, and CDR3 of the murine light chain regions comprise an amino acid sequence selected from the group consisting of the amino acid sequences of the CDR1, CDR2, and CDR3 regions shown in SEQ ID Nos: 4, 5 and 6, and conservative sequence modifications thereof. The antibody amino acid sequence can further optionally comprise at least one specified substitution, insertion or deletion as described herein or as known in the art. The non-binding regions of the antibody of the invention can include or be derived from germline antibody sequences of any mammal, such as but not limited to a human, a mouse, a rabbit, a rat, a rodent, a primate, or any combination thereof, and the like, or the antibody can be synthetic, or can be in other than an antibody scaffold, such as in a fibronection scaffold. The antibodies of the invention may include humanized forms of the murine antibody C775 in a variety of antibody isotypes, such as IgG1, (e.g., IgG1k), IgG2, IgG3, IgG4, IgM, IgA1, IgA2, IgAsec, IgD, and IgE.

Other particular antibodies of the invention include antibodies which bind to an epitope defined by antibody C775, and/or which compete for binding to the MCP-1 with antibody C775, or which have other functional binding characteristics exhibited by antibody C775. Such antibodies include, for example, those which bind to MCP-1 with a dissociation constant $(K_D)$ Of $10^{-7}$ M or less, such as of $10^{-8}$ M or less, $10^{-9}$M or less, $10^{-10}$ M or less, or even lower (e.g., $10^{-11}$ M or less). Such antibodies include those that competitively inhibit binding of the C775 antibody to human MCP-1.

The present invention also provides at least one isolated anti-MCP-1 antibody as described herein, wherein the antibody has at least one activity, such as, but not limited to inhibition of MCP-1 binding to chemokine receptors of the C—C family, in particular, the CCR2 receptor or, binding to CCR2 receptor expressing cells. An anti-MCP-1 antibody can thus be screened for a corresponding activity according to known methods, such as but not limited to, competition with the C775 antibody for at least one biological activity towards an MCP-1 protein and inhibition of CCR2 receptor downstream signalling. The isolated anti-MCP-1 antibody of the invention may have additional activities as defined herein which include the inhibition of MCP-1 stimulated monocyte chemotaxis or the reduction in intracellular calcium mobilization.

The present invention provides, in one aspect, isolated nucleic acid molecules comprising, complementary, or hybridizing to, a polynucleotide encoding the specific anti-MCP-1 antibodies described herein. Such nucleic acid molecules include those encoding all or a portion of a human monoclonal anti-MCP-1 antibody as described herein (e.g., which encode at least one light or heavy chain CDR of the antibody), as well as recombinant expression vectors which include such nucleic acids, and host cells transfected with such vectors. Methods of producing the antibodies by culturing such host cells are also encompassed by the invention. Particular nucleic acids provided by the invention comprise the nucleotide sequences which encode the heavy and light chains CDRs as shown in SEQ ID NOS: 12-14 and 15-17, respectively, of anti-MCP-1 antibody C775 and the nucleic acids which encode the complete variable region of the heavy or light chain, respectively, as shown in SEQ ID Nos: 10 and 11. The present invention further provides recombinant vectors comprising said anti-MCP-1 antibody nucleic acid molecules, host cells containing such nucleic acids and/or recombinant vectors, as well as methods of making and/or using such antibody nucleic acids, vectors and/or host cells.

The present invention also provides at least one method for expressing at least one anti-MCP-1 antibody as described herein, or anti-MCP-1 anti-idiotype antibody as described herein, in a host cell, comprising culturing a host cell as described herein under conditions wherein at least one anti-MCP-1 antibody is expressed in detectable and/or recoverable amounts.

The present invention also provides at least one composition comprising (a) an isolated anti-MCP-1 antibody encoding nucleic acid and/or antibody as described herein; and (b) a suitable carrier or diluent. The carrier or diluent can optionally be pharmaceutically acceptable, according to known carriers or diluents. The composition can optionally further comprise at least one further compound, protein or composition.

The present invention provides at least one anti-MCP-1 antibody method or composition, for administering a therapeutically effective amount to modulate or treat at least one MCP-1 related condition in a cell, tissue, organ, animal or patient and/or, prior to, subsequent to, or during a related condition, as known in the art and/or as described herein. Compositions, e.g., pharmaceutical compositions, comprising a combination of at least one anti-human MCP-1 antibody, or antigen-binding portion thereof, and at least one other therapeutic agent are also provided for by the methods of the invention. Thus, the combination provides multiple therapies tailored to provide the maximum therapeutic benefit. The present invention further provides diagnostic compositions/kits, comprising an at least one anti-MCP-1 antibody, or an antigen-binding portion thereof.

Accordingly, antibodies of the present invention can be used to treat and/or prevent a variety of MCP-1 mediated diseases by administering a suitable dosage (or series of dosages) of the antibodies to patients suffering from such diseases. Exemplary diseases that can be treated (e.g., ameliorated) or prevented using the methods and compositions of the invention include, but are not limited to, cancers, inflammatory or immuned mediated disorders, and diseases characterized by excessive fibrosis. They can be coadministered simultaneously with such agents (e.g., in a single composition or separately) or can be administered before or after administration of such agents. Human antibodies of the invention also can be administered in conjunction with radiation therapy or other treatment modalities.

In a particular embodiment of the invention, the patient can be additionally treated with a chemotherapeutic agent, radiation, or an agent that modulates, e.g., enhances, the expression or activity of an Fc receptor, such as a cytokine. Such agents can include chemotherapeutic agents, such as doxorubicin (Adriamycin), cisplatin, placlitaxol, methotrexate, bleomycin sulfate, carmustine, chlorambucil, cyclophosphamide, 5-fluorouracil, gemcitabine and combinations thereof. Typical cytokines for administration during treatment include granulocyte colony-stimulating fact or (G-CSF), granulocyte macrophage colony-stimulating factor (GM-CSF), interferon-y (IFN-y), and interleukin 2 (IL-2).

In yet another aspect of the invention, the anti-MCP-1 antibodies are derivatized, linked to or co-expressed with another functional molecule, e.g., another peptide or protein (e.g., an Fab' fragment). For example, an antibody or antigen-binding portion of the invention can be functionally linked (e.g., by chemical coupling, genetic fusion, noncovalent association or otherwise) to one or more other molecular entities, such as another antibody (e.g., to produce a bispecific or a multispecific antibody), a cytotoxin, a cellular ligand or an antigen. Accordingly, present invention encompasses a large variety of antibody conjugates, bi- and multispecific molecules, and fusion proteins, all of which bind to MCP-1 expressing cells and which target other molecules to the cells, or which bind to MCP-1 and to other molecules or cells.

For use in in vivo treatment and prevention of MCP-1 mediated diseases, human antibodies of the present invention are administered to patients (e.g., human subjects) at therapeutically effective dosages. The treatment may act directly on tumor cells expressing, secreting, or displaying MCP-1 on the cell surface or may act by a wholly different route such as to inhibit host effects stimulated by MCP-1 the lead to complex process such angiogenesis and thus inhibit the growth of cells where growth is mediated by angiogenesis using any suitable route of administration for antibody-based clinical products as are well known in the art, such as by injection or infusion.

In yet another aspect, the present invention provides a transgenic nonhuman animal, such as a transgenic mouse, which expresses a fully human monoclonal antibody that binds to MCP-1. In a particular embodiment, the transgenic nonhuman animal is a transgenic mouse having a genome comprising a human heavy chain transgene and a human light chain transgene encoding all or a portion of an anti-MCP-1 antibody of the invention. To generate anti-human MCP-1 antibodies, the transgenic nonhuman animal can be immunized with a purified or enriched preparation of MCP-1 antigen and/or cells expressing MCP-1. Alternatively, the nonhuman animal, e.g. a goat, may be transfected with the nucleic acids of the invention in such a manner as to cause the non-human transfected animal (transgenic animal) to express and secrete the anti-MCP-1 antibody of the invention.

Accordingly, in another embodiment, the invention provides isolated cells derived from an animal as described above, e.g., a transgenic mouse, which express human anti-MCP-1 antibodies. The isolated B-cells can then be immortalized by fusion to an immortalized cell to provide a source (e.g., a hybridoma) of human anti-MCP-1 antibodies. Such hybridomas (i.e., which produce human anti-MCP-1 antibodies) are also included within the scope of the invention.

The present invention further provides at least one anti-MCP-1 antibody method or composition, for diagnosing at least one MCP-1 protein related condition in a cell, tissue, organ, animal or patient and/or, prior to, subsequent to, or during a related condition, as known in the art and/or as described herein.

The present invention further provides at least one anti-MCP-1 anti-idiotype antibody to at least one MCP-1 antibody of the present invention. The anti-idiotype antibody includes any protein or peptide containing molecule that comprises at least a portion of an immunoglobulin molecule, such as but not limited to at least one complementarity determinng region (CDR) of a heavy or light chain or a ligand binding portion thereof, a heavy chain or light chain variable region, a heavy chain or light chain constant region, a framework region, or any portion thereof, that can be incorporated into an antibody of the present invention. An anti-idiotype antibody of the invention can include or be derived from any mammal, such as but not limited to a human, a mouse, a rabbit, a rat, a rodent, a primate, and the like.

The present invention provides, in one aspect, isolated nucleic acid molecules comprising, complementary, or hybridizing to, a polynucleotide encoding at least one anti-MCP-1 anti-idiotype antibody, comprising at least one specified sequence, domain, portion or variant thereof. The present invention further provides recombinant vectors comprising said MCP-1 anti-idiotype antibody encoding nucleic acid molecules, host cells containing such nucleic acids and/or recombinant vectors, as well as methods of making and/or using such anti-idiotype antiobody nucleic acids, vectors and/or host cells.

DETAILED DESCRIPTION OF THE INVENTION

Figure 1:
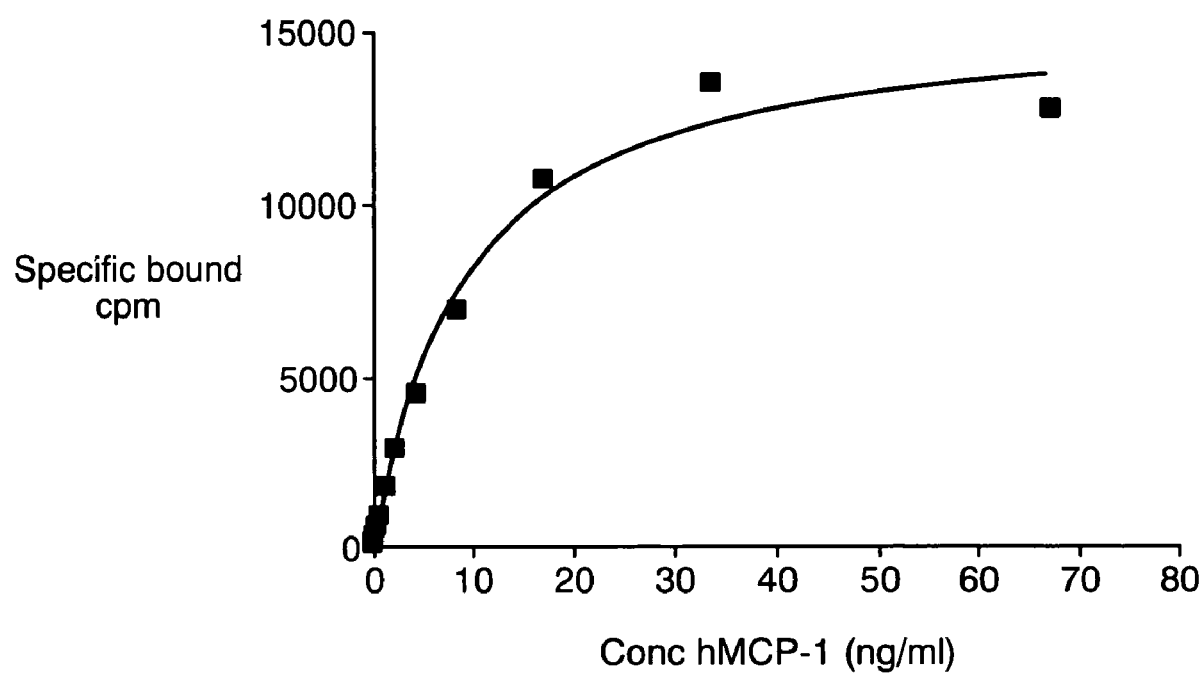
FIG. 1 shows a graph displaying the relationship of radiolabeled MCP-1 binding to concentration in an in vitro assay and the calculation of the Kd therefrom.

The present invention provides isolated, recombinant and/or synthetic anti-human MCP-1 monoclonal antibodies and MCP-1 anti-idiotype antibodies thereto, as well as compositions and encoding nucleic acid molecules comprising at least one polynucleotide encoding at least one anti-MCP-1 antibody or anti-idiotype antibody. The present invention further includes, but is not limited to, methods of making and using such nucleic acids and antibodies and anti-idiotype antibodies, including diagnostic and therapeutic compositions, methods of producing such antibodies, and devices comprising such antibodies. Therapies of the invention employ isolated monoclonal antibodies and/or related compositions containing the antibodies which bind to an epitope present on MCP-1 and are capable of inhibiting or blocking the various direct and indirect biological actions associated with MCP-1-containing complexes, regardless of the protein subunit or other biological molecule to which it is associated. In a particular embodiment exemplified herein, the antibodies are selected to be higly specific to MCP-1 and not specific for MCP-2, MCP-3, MCP-4, or eotaxin. Accordingly, aspects of the invention include not only antibodies, antibody fragments, and pharmaceutical compositions thereof, but also nonhuman transgenic animals, B-cells and hybridomas which produce monoclonal antibodies. Methods of using the antibodies of the invention to detect a cell expressing MCP-1, prevent MCP-1 binding to a receptor on a cell surface or in soluble form, to inhibit signaling of a MCP-1 binding receptor, or inhibit the downstream action of said signalling such as but not limited to differentiation and/or motility of a cell expressing MCP-1 binding receptor or secretion of a protein product by a cell expressing MCP-1 binding receptors, either in vitro or in vivo, are also encompassed by the invention.

In order that the present invention may be more readily understood, certain terms are first defined. Additional definitions are set forth throughout the detailed description.

As used herein, an "antibody" includes whole antibodies and any antigen binding fragment or a single chain thereof. Thus the antibody includes any protein or peptide containing molecule that comprises at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein, which can be incorporated into an antibody of the present invention. The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments to a preselected target. Examples of binding fragments encompassed within the term "antigen binding portion" of an antibody include (i) a Fab fragment, a monovalent fragment consisting of the VL, VH, CL and CH, domains; (ii) a F(ab')2 fragment, a bivalent fragment comprising two Fab fragments linked by a disulfide bridge at the hinge region; (iii) a Fd fragment consisting of the VH and CH, domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426, and Huston et al. (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Conversely, libraries of scFv constructs can be used to screen for antigen binding capability and then, using conventional techniques, spliced to other DNA encoding human germline gene sequences. One example of such a library is the "HuCAL: Human Combinatorial Antibody Library" (Knappik, A. et al. J Mol Biol (2000) 296 (1):57-86).

The term "epitope" means a protein determinant capable of specific binding to an antibody. Epitopes usually consist of chemically active surface groupings of molecules such as amino acids or sugar side chains and usually have specific three-dimensional structural characteristics, as well as specific charge characteristics. Conformational and nonconformational epitopes are distinguished in that the binding to the former but not the latter is lost in the presence of denaturing solvents. The term "native conformational epitope" or "native protein epitope" are used interchangeably herein, and include protein epitopes resulting from conformational folding of the MCP-1 molecule which arise when amino acids from differing portions of the linear sequence of the MCP-1 molecule come together in close proximity in 3-dimensional space. Such conformational epitopes are distributed on the extracellular side of the plasma membrane.

The term "bispecific molecule" is intended to include any agent, e.g., a protein, peptide, or protein or peptide complex, which has two different binding specificities. For example, the molecule may bind to, or interact with, (a) a cell surface antigen and (b) an Fc receptor on the surface of an effector cell. The term "multispecific molecule" or "heterospecific molecule" is intended to include any agent, e.g. a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to cell surface antigens, such as MCP-1, and to other targets, such as Fc receptors on effector cells.

Antibodies are naturally "bivalent antibodies", however, the term also includes diabodies. Diabodies, for example, are bivalent antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (I 994) Structure 2:1121-1123). "Multivalent" antibodies include two or more binding domains which may all be of the same specificity or may have multiple specificities.

"Chimeric antibodies" are those antibodies that retain distinct domains, usually the variable domain, from one species and the remainder from another species; e.g. mouse-human chimeras.

The term "human antibody", as used herein, is intended to include antibodies having variable and constant regions derived from or closely matching human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo such as during the recombination of V, D, and J segments of the human heavy chain). Thus as used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially similar to those encoded by human germline antibody genes. Human antibodies have been classified into groupings based on their amino acid sequence similarities, see e.g. http://people.cryst.bbk.ac.uk/~ubcg07s/. Thus, using a sequence similarity search, an antibody with similar linear sequence can be chosen as a template to select or create human or humanized antibodies.

"Humanization" (also called Reshaping or CDR-grafting) includes established techniques for reducing the immunogenicity of monoclonal antibodies (mAbs) from xenogeneic sources (commonly rodent) and for improving affinity or the effector functions (ADCC, complement activation, C1q binding). The engineered mAb can be produced using the techniques of molecular biology, using phage displayed randomized sequences, or synthesized de novo. For example, in order to humanize an antibody with incorporated the CDR regions from a nonhuman species, the design might include variations such as conservative amino acid substitutions in residues of the CDRs, and back substitution of residues from the nonhuman mAb into the human framework regions (backmutations). The positions can be discerned or identified by sequence comparison methods, consensus seqeuence analysis, or structural analysis of the variable regions' 3D structure. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR (framework) residues can be selected and combined from the consensus and import sequences so that the desired antibody characteristic, such as increased affinity for the target antigen(s), is achieved. As the datasets of known parameters for antibody structures increases, so does the sophistication and refinement of these techniques. Another approach to humanization is to modify only surface residues of the rodent sequence with the most common residues found in human mabs and has been termed "resurfacing" or "veneering". Known human Ig sequences are disclosed, e.g., www.ncbi.nlm.nih.gov/entrez/query.fcgi; www.ncbi.nih-.gov/igblast; www.kabatdatabase.com/top.html; www.antibodyresource.com/onlinecomp.html; www.appliedbiosystems.com; www.biodesign.com; antibody.bath.ac.uk; http://www.unizh.ch/~antibody/; www.cryst.bbk.ac.uk/~ubcg07s; Kabat et al., Sequences of Proteins of Immunological Interest, U.S. Dept. Health (1983), each entirely incorporated herein by reference. Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239: 1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766,886, 5,714,352, 6,204,023, 6,180,370, 5,693,762, 5,530,101, 5,585,089, 5,225,539; 4,816,567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

The term "CDR" refers to the complementarity determining region or hypervariable region amino acid residues of an antibody which are responsible for antigen-binding. The hypervariable region or CDRs of the human IgG subtype of antibody comprise amino acid residues from residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, 5th Ed. Public Health Service, National Institutes of Health, Bethesda, Md. (1991)] and/or those residues from a hypervariable loop (i.e., residues 26-32 (L1), 50-52 (L2) and 91-96 (L3) in the light chain variable domain and 26-32 (H1), 53-55 (H2) and 96-101 (H3) in the heavy chain variable domain as described by [Chothia et al., J. Mol. Biol. 196: 901-917 (1987)]. Framework or FR residues are those variable domain residues other than and bracketing the hypervariable regions.

The term "MCP-1" is used herein to mean "Monocyte chemoattractant protein 1", monocyte chemotactic and activating factor; monocyte secretory protein JE (homologous to mouse Sig-je); small inducible cytokine subfamily A (Cys-Cys) member 2 SCYA2, or "human JE protein" and include all of the variants, isoforms and species homologs of MCP-1. Accordingly, the antibodies of the invention may, in certain cases, cross-react with MCP-1 from species other than human. In other cases, the antibodies may be completely specific for human MCP-1 and not exhibit species or other types of cross-reactivity.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences.

The term "recombinant antibody", as used herein, includes all antibodies that are prepared, expressed, created or isolated by recombinant means, such as (a) antibodies isolated from an animal or a hybridoma prepared therefrom (described further in Section I, below), (b) antibodies isolated from a host cell transformed to express the antibody, e.g., from a transfectoma, (c) antibodies isolated from a recombinant, combinatorial human or other species antibody library, and (d) antibodies prepared, expressed, created or isolated by any other means that involve splicing of immunoglobulin gene sequences to other DNA sequences.

An "isolated antibody," as used herein, is intended to refer to an antibody which is substantially free of other antibodies having different antigenic specificities (e.g., an isolated antibody that specifically binds to MCP-1 is substantially free of antibodies that specifically bind antigens other than MCP-1). An isolated antibody that specifically binds to an epitope, isoform or variant of human MCP-1 may, however, have cross-reactivity to other related antigens, e.g., from other species (e.g., MCP-1 species homologs). Moreover, an isolated antibody may be substantially free of other cellular material and/or chemicals. In one embodiment of the invention, a combination of "isolated" monoclonal antibodies having different specificities are combined in a well defined composition.

As used herein, the term "high affinity" for an antibody refers to an antibody having a $K_D$ Of $10^{-8}$ M or less, more preferably $10^{-9}$ M or less and even more preferably $10^{-10}$ M or less. However, "high affinity" binding can vary for other antibody isotypes. For example, "high affinity" binding for an IgM isotype refers to an antibody having a $K_D$ of $10^{-7}$ M or less, more preferably $10^{-8}$ M or less. The term "Kdis" or "$K_D$," or 'Kd' as used herein, is intended to refer to the dissociation rate of a particular antibody-antigen interaction. The "$K_D$", is the ratio of the rate of dissociation ($k_2$), also called the "off-rate ($k_{off}$)", to the rate of association rate ($k_1$) or "on-rate ($k_{on}$)". Thus, $K_D$ equals k2/k1 or $k_{off}/k_{on}$ and is expressed as a molar concentration (M). It follows that the smaller Kd, the stronger the binding. So $10^{-6}$M (or 1 mM) indicates weak binding compared to $10^{-9}$ M (or 1 nM).

As used herein, "specific binding" refers to antibody binding to a predetermined antigen. Typically, the antibody binds with a dissociation constant ($K_D$) of $10^{-7}$ M or less, and binds to the predetermined antigen with a $K_D$ that is at least twofold less than its $K_D$ for binding to a non-specific antigen (e.g., BSA, casein, or any other specified polypeptied) other than the predetermined antigen. The phrases "an antibody recognizing an antigen" and "an antibody specific for an antigen" are used interchangeably herein with the term "an antibody which binds specifically to an antigen". As used herein "highly specific" binding means that the relative $K_D$ of the antibody for the specific target epitope is at least 10-fold less than the $K_D$ for binding that antibody to other ligands.

As used herein, "isotype" refers to the antibody class (e.g., IgM or IgG) that is encoded by heavy chain constant region genes. Some antibody classes further encompass subclasses which are also encoded by the heavy chain constant regions and further decorated by oligosaccharides at specific residues within the contant region domains (e.g. IgG1, IgG2, IgG3 and IgG4) which further impart biological functions to the antibody.

The term "nucleic acid molecule", as used herein, is intended to include DNA molecules and RNA molecules. A nucleic acid molecule may be single-stranded or double-stranded, but preferably is double-stranded DNA.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Citations

All publications or patents cited herein are entirely incorporated herein by reference as they show the state of the art at the time of the present invention and/or to provide description and enablement of the present invention. Publications refer to any scientific or patent publications, or any other information available in any media format, including all recorded, electronic or printed formats. The following references are entirely incorporated herein by reference: Ausubel, et al., ed., Current Protocols in Molecular Biology, John Wiley & Sons, Inc., NY, N.Y. (1987-2001); Sambrook, et al., Molecular Cloning: A Laboratory Manual, $2^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001).

Abbreviations:
CDR—complementarity determining region
HC—heavy chain
LC—light chain
Ig—immunoglobulin
Mab—monoclonal antibody
PEG—polyethylene glycol
VL—Variable light chain
VH—Variable heavy chain 1. Antibodies of the Invention An MCP-1 antibody of the invention is an antibody that affects the MCP-1 ligand, such as but not limited to where such antibody modulates, decreases, increases, antagonizes, angonizes, mitigates, aleviates, blocks, inhibits, abrogates and/or interferes with at least one MCP-1 activity or binding, or with MCP-1 activity or binding, in vitro, in situ and/or in vivo. As a non-limiting example, a suitable anti-MCP-1 antibody, specified portion or variant of the present invention can bind at least one MCP-1 polypeptide, or specified portions, variants or domains thereof. A suitable anti-MCP-1 antibody, specified portion, or variant can also optionally affect at least one of MCP-1 activity or function, such as but not limited to, RNA, DNA or protein synthesis, protein release, MCP-1 receptor signaling, membrane MCP-1 cleavage, MCP-1 activity, MCP-1 production and/or synthesis.

In one embodiment, the anti-human MCP-1 antibody, or portion thereof, includes the nucleotide or amino acid sequence of C775, as well as heavy chain (VH) and light chain (VL) variable regions having the amino acid sequences shown in SEQ ID NOs: 7 and 8, respectively, and nucleotide sequences encoding them, e.g., but not limited to, SEQ ID Nos: 10 and 11. In another embodiment of the invention, the antibody binds to MCP-1 protein and, in addition, the antibodies or antigen binding fragments or portions thereof may be selected for their retention of other functional properties of antibodies of the invention, such as:

binding to human MCP-1 in ELISA;

lack of specific binding to human MCP-2, 3, 4 and human Eotaxin 1, 2 and 3;

inhibition of human MCP-1 binding to its human receptor CCR2 on Thp-1 cells with IC50 which is less than or equal to that of murine antibody C775;

inhibition of human MCP-1 mediated chemotaxis of THP-1 cells with an IC50 which is less than or equal to that of Fab C775;

inhibition of human MCP-1 mediated activity in a second bioassay (e.g. Ca2+ mobilization)

binding to human MCP-1 with $K_d$ of less than 0.5 nM;

binding to cynomolgus monkey MCP-1 with a $K_D$ of less than 20 nM, and more preferably, less than 10 nM;

inhibition of native human MCP-1 and synthetic MCP-1 with similar potency; and retention of the above activities as an IgG which are comparable to the IgG C775.

In another aspect of the invention, the structural features of the C775 binding domain, are used to create structurally related human anti-MCP-1 antibodies that retain at least one functional property of the antibodies of the invention, such as binding to MCP-1. More specifically, one or more CDR regions of C775 can be combined recombinantly with known human framework regions and CDRs to create additional, recombinantly-engineered, human anti-MCP-1 antibodies of the invention.

Since it is well known in the art that antibody heavy and light chains CDR domains play a particularly important role in the binding specificity/affinity of an antibody for an antigen, the recombinant antibodies of the invention prepared as set forth above preferably comprise the heavy and light chain CDR3s of C775. The antibodies further can comprise the CDR2s of C775. The antibodies further can comprise the CDR1s of C775. Accordingly, the invention further provides anti-MCP-1 antibodies comprising: (1) human heavy chain framework regions, a human heavy chain CDR1 region, a human heavy chain CDR2 region, and a human heavy chain CDR3 region, wherein the human heavy chain CDR3 region is selected from the CDR3s of C775 as shown in SEQ ID NO: 3, and (2) human light chain framework regions, a human light chain CDR1 region, a human light chain CDR2 region, and a human light chain CDR3 region, wherein the human light chain CDR3 region is selected from the CDR3s of C775 as shown in SEQ ID NO: 6, wherein the antibody binds MCP-1. The antibody may further comprise the heavy chain CDR2 and/or the light chain CDR2 of C775. The antibody may further comprise the heavy chain CDR1 and/or the light chain CDR1 of C775.

As a non-limiting example, the antibody or antigen-binding portion or variant can comprise at least one of the heavy chain CDR3 having the amino acid sequence of SEQ ID NO: 3, and/or a light chain CDR3 having the amino acid sequence of SEQ ID NO:6. In a particular embodiment, the antibody or antigen-binding fragment can have an antigen-binding region that comprises at least a portion of at least one heavy chain CDR (i.e., CDR1, CDR2 and/or CDR3) having the amino acid sequence of the corresponding CDRs 1, 2 and/or 3 (e.g., SEQ ID NOS: 1, 2, and/or 3). In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3 (e.g., SEQ ID NOS: 4, 5, and/or 6). In a preferred embodiment the three heavy chain CDRs and the three light chain CDRs of the anitbody or antigen-binding fragment have the amino acid sequence of the corresponding CDR of at least one of mAb C775, OR OTHER NAMES, as described herein. Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

```
HC CDR1      DYYIN (SEQ ID NO:1)

HC CDR2      RIYPGTGNTYYNENFKG (SEQ ID NO:2)

HC CDR3      SGSTVVGNYYGMDY (SEQ ID NO:3)

LC CDR1      KASQSVSNDVA (SEQ ID NO:4)

LC CDR2      YASNRYT (SEQ ID NO:5)

LC CDR3      QQDYSSPWT (SEQ ID NO:6)
```

Preferably, the CDR1, 2, and/or 3 of the engineered antibodies described above comprise the exact amino acid sequence(s) as those of C775 disclosed herein. However, the ordinarily skilled artisan will appreciate that some deviation from the exact CDR sequences of C775 may be possible while still retaining the ability of the antibody to bind MCP-1 effectively (e.g., conservative substitutions). Accordingly, in another embodiment, the engineered antibody may be composed of one or more CDRs that are, for example, 90%, 95%, 98% or 99.5% identical to one or more CDRs of C775. In addition to simply binding MCP-1, engineered antibodies such as those described above may be selected for their retention of other functional properties of antibodies of the invention, such as the ability to inhibit angiogenesis resulting in growth inhibition of tumor cells in vivo.

Human monoclonal antibodies of the invention can be tested for binding to MCP-1 by, for example, standard ELISA.

To determine if the selected human anti-MCP-1 monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using MCP-1 coated-ELISA plates. Biotinylated mAb binding can be detected with a strep-avidin-alkaline phosphatase probe.

To determine the isotype of purified antibodies, isotype ELISAs can be performed. In order to demonstrate binding of monoclonal antibodies to live cells expressing the MCP-1, flow cytometry can be used. Anti-MCP-1 human IgGs can be further tested for reactivity with MCP-1 antigen by Western blotting.

In another aspect of the invention, the structural features of an anti-MCP-1 antibodies of the invention, C775, are used to create structurally related anti-MCP-1 antibodies that retain at least one functional property of the antibodies of the invention, such as binding to MCP-1. More specifically, one or more CDR regions of C775 can be combined recombinantly with known human framework regions and CDRs to create additional, recombinantly-engineered, human anti-MCP-1 antibodies of the invention.

Depending on the use intended for the antibodies of the invention, the antibody may be re-engineered so as to optimize stability, solubility, in vivo half-life, or ability to bind addition targets. Genetic engineering approaches as well as chemical modification to accomplishing any or all of the aforementioned changes in properties are known in the art.

Whereas the variable domains of each pair of light and heavy chains are the specific ligand binding domains of the antibody, other molecules, known as effector molecules or cells, bind to other sites in the remainder of the molecule, ie other than the antigen binding sites. Due to their relatively invariant nature, as compared to the binding domain sequences, these domains are generally referred as "the constant portion" of an antibody, such sites being located particularly in the Fc region constituted by the portions of the heavy chains extending beyond the ends of the light chains.

The addition, removal, or modification of the constant regions of the antibody are known to play a particularly crucial role in the bioavailability, distribution, and half-life of therapeutically administered antibodies. The antibody class and subclass, encoded by the Fc or constant region of the antibody, when present, imparts important additional properties. Thus, MCP-1 binding antibodies with reconfigured, redesigned, or otherwise altered constant domains are encompassed by the anti-MCP-1 antibody compositions of the invention.

The effector functions mediated by the antibody Fc region can be divided into two categories: (1) effector functions that operate after the binding of antibody to an antigen (these functions involve the participation of the complement cascade or Fc receptor (FcR)-bearing cells); and (2) effector functions that operate independently of antigen binding (these functions confer persistence in the circulation and the ability to be transferred across cellular barriers by transcytosis (Ward and Ghetie, Therapeutic Immunology 2:77-94 (1995). Cellular responses depend on activation by binding of Ab-Ag complexes and by downstream sequelae caused by the release of cell mediators as a result of Ab-Ag complex binding to effector cells. These cellular responses include neutralization of target, opsonization and sensitization (if antigen is displayed on the surface of a cell), sensitization of mast cells, and activation of complement. For cellular targets, that is cell surface antigens, these effector functions lead to what is commonly known as Antibody Directed Cellular cytotoxicity (ADCC) and Complement-mediated cytotoxicity (CDC).

There are five major classes or isotypes of immunoglobulins: IgA, IgD, IgE, IgG and IgM, and several of these may be further divided into subclasses (subtypes), e.g. IgG1, IgG2, IgG3, and IgG4; IgA1, IgA2, and IgAsec. The light chains are of two classes (kappa and lambda). The heavy chain constant regions that correspond to the different classes of immunoglobulins are called α, δ, ε, γ, and μ, respectively. Of the various human immunoglobulin classes, only human IgG1, IgG2, IgG3 and IgM are known to activate complement; and human IgG1 and IgG3 mediate ADCC more effectively than IgG2 and IgG4. The antibodies of the invention may include chimeric or humanized forms of the murine antibody C775 in a variety of human antibody isotypes and subtypes, such as, IgG1kappa, IgG2, IgG4, IgM, and IgA1.

Accordingly, in another embodiment, the invention provides a method for preparing an anti-MCP-1 antibody comprising: preparing an antibody comprising (1) human heavy chain framework regions and human heavy chain CDRs, wherein at least one of the human heavy chain CDRs comprises an amino acid sequence selected from the amino acid sequences of CDRs shown in SEQ ID NOs: 1-3; and (2) human light chain framework regions and human light chain CDRs, wherein at least one of the human heavy chain CDRs comprises an amino acid-sequence selected from the amino acid sequences of CDRs shown in SEQ ID NOs: 4-6; wherein the antibody retains the ability to bind to MCP-1.

The ability of the antibody to bind MCP-1 can be determined using standard binding assays, such as those set forth in the Examples (e.g., an ELISA).

The antibodies of the invention can bind human MCP-1 subunit with a wide range of affinities ($K_D$). In a preferred embodiment, at least one human mAb of the present invention can optionally bind human MCP-1 subunit with high affinity. For example, a human mAb can bind human MCP-1 with a $K_D$ equal to or less than about $10^{-7}$ M, such as but not limited to, 0.1-9.9 (or any range or value therein) X $10^{-7}$, $10^{-8}$, $10^{-9}$, $10^{-10}$, $10^{-11}$, $10^{-12}$, $10^{-13}$ M or any range or value therein.

The affinity or avidity of an antibody for an antigen can be determined experimentally using any suitable method. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., $K_D$, IC50) are preferably made with standardized solutions of antibody and antigen, and a standardized buffer, such as the buffer described herein.

Preferably, the antibody or antigen-binding fragment of the invention binds human MCP-1 and, thereby partially or substantially neutralizes at least one biological activity of the protein. An antibody, or specified portion or variant thereof, that partially or preferably substantially neutralizes at least one biological activity of at least one MCP-1 protein or fragment can bind the protein or fragment and thereby inhibit activities mediated through the binding of MCP-1 to its ligand or through other MCP-1 or mediated mechanisms. As used herein, the term "neutralizing antibody" refers to an antibody that can inhibit an MCP-1 activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-MCP-1 antibody to inhibit an MCP-1 activity is preferably assessed by at least one suitable MCP-1 protein or receptor assay, as described herein and/or as known in the art. An antibody of the invention can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4.

At least one antibody of the invention binds at least one specified epitope specific to at least one SEQ ID NO: 9, human MCP-1, fragment, portion or any combination thereof. The at least one epitope can comprise at least one antibody binding region that comprises at least one portion of said protein, which epitope is preferably comprised of at least one extracellular, soluble, hydrophillic, external or cytoplasmic portion of said protein. The epitope can comprise at least one antibody binding region that comprises at least one portion of said protein, which epitope is preferably comprised of at least 1-5 amino acids of at least one portion of an MCP-1, such as but not limited to: 24-99, 30-99, 34-99, 24-90, 30-90, or 34-90 of SEQ ID NO: 9, respectively thereof, or such as but not limited to, at least one functional, extracellular, soluble, hydrophilic, external or cytoplasmic domain of said MCP-1 protein, or any portion thereof. Particularly preferred are antibodies which bind to substantially the same epitope on the MCP-1 defined by the epitope of C775, and/or which compete for binding to MCP-1 with antibody C775, or which have other functional binding characteristics exhibited by antibody C775.

As previously stated, the invention also relates to antibodies, antigen-binding fragments, immunoglobulin chains and CDRs comprising amino acids in a sequence that is substantially the same as an amino acid sequence described herein. Preferably, such antibodies bind MCP-1 with high affinity (e.g., $K_D$ less than or equal to about $10^{-9}$ M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g, charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

An anti-MCP-1 antibody of the present invention can include one or more amino acid substitutions, deletions or additions, either from natural mutations or human manipulation, as specified herein.

Amino acids in an anti-MCP-1 antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to at least one MCP-1 neutralizing activity. Sites that are critical for antibody binding can also be identified by structural analysis such as crystallization, nuclear magnetic resonance or photoaffinity labeling (Smith, et al., J. Mol. Biol. 224:899-904 (1992) and de Vos, et al., Science 255:306-312 (1992)).

Anti-MCP-1 antibodies of the present invention can include, but are not limited to, at least one portion, sequence or combination selected from 5 to all of the contiguous amino acids of at least one of SEQ ID NOS: 1, 2, 3, 4, 5, 6.

A(n) anti-MCP-1 antibody can further optionally comprise a polypeptide of at least one of 70-100% of the contiguous amino acids of at least one of SEQ ID NOS: 7, 8.

In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of SEQ ID NOS: 7, 8. For example, the amino acid sequence of a light chain variable region can be compared with the sequence of SEQ ID NO: 8, or the amino acid sequence of a heavy chain CDR3 can be compared with SEQ ID NO: 7. Preferably, 70-100% amino acid identity (i.e., 90, 91, 92, 93, 94, 95, 96, 97, 98, 99, 100 or any range or value therein) is determined using a suitable computer algorithm, as known in the art.

Exemplary heavy chain and light chain variable regions sequences are provided in SEQ ID NOS: 7, 8. The antibodies of the present invention, or specified variants thereof, can comprise any number of contiguous amino acid residues from an antibody of the present invention, wherein that number is selected from the group of integers consisting of from 10-100% of the number of contiguous residues in an anti-MCP-1 antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and preferably at least 50%, 60%, or 70%, and most preferably at least 80%, 90%, or 95%-100% of that of the parent antibody, C775. Methods of assaying and quantifying measures of enzymatic activity and substrate specificity, are well known to those of skill in the art.

2. Generation of Anti-MCP-1 Antibodies

Anti-MCP-1 antibodies of the present invention can be optionally produced by a variety of techniques, including the standard somatic cell hybridization technique (hybridoma method) of Kohler and Milstein (1975) Nature 256:495. In the hybridoma method, a mouse or other appropriate host animal, such as a hamster or macaque monkey, is immunized as described herein to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice., pp. 59-103 (Academic Press, 1986)).

The anti-MCP-1 antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-MCP-1 antibody can be isolated from such animals and immortalized using suitable methods, such as the methods described herein.

The use of transgenic mice carrying human immunoglobulin (Ig) loci in their germline configuration provide for the isolation of high affinity fully human monoclonal antibodies directed against a variety of targets including human self antigens for which the normal human immune system is tolerant (Lonberg, N. et al., U.S. Pat. No. 5,569,825, U.S. Pat. No. 6,300,129 and 1994, Nature 368:856-9; Green, L. et al., 1994, Nature Genet. 7:13-21; Green, L. & Jakobovits, 1998, Exp. Med. 188:483-95; Lonberg, N and Huszar, D., 1995, Int. Rev. Immunol. 13:65-93; Kucherlapati, et al. U.S. Pat. No. 6,713,610; Bruggemann, M. et al., 1991, Eur. J. Immunol. 21:1323-1326; Fishwild, D. et al., 1996, Nat. Biotechnol. 14:845-851; Mendez, M. et al., 1997, Nat. Genet. 15:146-156; Green, L., 1999, J. Immunol. Methods 231:11-23; Yang, X. et al., 1999, Cancer Res. 59:1236-1243; Brüggemann, M. and Taussig, M J., Curr. Opin. Biotechnol. 8:455-458, 1997; Tomizuka et al. WO02043478). The endogenous immunoglobulin loci in such mice can be disrupted or deleted to eliminate the capacity of the animal to produce antibodies encoded by endogenous genes. In addition, companies such as Abgenix, Inc. (Freemont, Calif.) and Medarex (San Jose, Calif.) can be engaged to provide human antibodies directed against a selected antigen using technology as described above.

Preparation of immunogenic antigens, and monoclonal antibody production can be performed using any suitable technique such as recombinant protein production. The immunogenic antigens can be administered to an animal in the form of purified protein, or protein mixtures including whole cells or cell or tissue extracts, or the antigen can be formed de novo in the animal's body from nucleic acids encoding said antigen or a portion thereof.

Immunization with antigen can be optionally accompanied by addition of an adjuvant, such as complete Freund's adjuvant. The immune response can be monitored over the course of the immunization protocol with plasma samples being obtained by retroorbital bleeds. The plasma can be screened by ELISA (as described below), and mice with sufficient titers of anti-MCP-1 immunoglobulin can be used for fusions. Mice can be boosted intravenously with antigen 3 days before sacrifice and removal of the spleen. It is expected that 2-3 fusions for each antigen may need to be performed. Several mice will be immunized for each antigen.

To generate hybridomas producing monoclonal antibodies to MCP-1, splenocytes and lymph node cells from immunized mice can be isolated and fused to an appropriate immortalized cell line, such as a mouse myeloma cell line. The resulting hybridomas can be screened for the production of antigen-specific antibodies.

A suitable immortal cell line incapable of producing immuoglobuling chains is selected as a fusion partner, e.g., a myeloma cell line such as, but not limited to, Sp2/0 and derivative cell lines, NS1 and derivatives, especially NSO engineered NSO lines such as GS-NSO, AE-1, L.5, P3X63Ag8.653, U937, MLA 144, ACT IV, MOLT4, DA-1, JURKAT, WEHI, K-562, COS, RAJI, NIH 3T3, HL-60, MLA 144, NAMAIWA, NEURO 2A, CHO, PerC.6, YB2/0 or the like, or heteromyelomas, fusion products thereof, or any cell or fusion cell derived therefrom, or any other suitable cell line as known in the art (Birch et al. 1994. Biologics 22:127-133). The fused cells (hybridomas) or recombinant cells can be isolated using selective culture conditions or other suitable known methods, and cloned by limiting dilution or cell sorting, or other known methods. Cells which produce antibodies with the desired specificity can be detected by a suitable assay (e.g., ELISA) and selected for manipulation.

Other suitable methods of generating or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; Biolnvent, Lund, Sweden; Dyax Corp., Enzon, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350,260(May 12, 1994); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); EP 614 989 (MorphoSys); WO95/16027 (Biolnvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723, 323, 5,763,192, 5,814,476, 5,817,483, 5,824,514, 5,976,862, WO 86/05803, EP 590689 (Ixsys, now Applied Molecular Evolution (AME), each entirely incorporated herein by reference) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (May 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Screening antibodies for specific binding to similar proteins or fragments can also be conveniently achieved using peptide display libraries. This method involves the screening of large collections of peptides for individual members having the desired function or structure. Antibody screening using peptide display libraries is well known in the art. The displayed peptide sequences can be from 3 to 5000 or more amino acids in length, frequently from 5-100 amino acids long, and often from about 8 to 25 amino acids long. Peptide display libraries, vector, and screening kits are commercially available from such suppliers as Invitrogen (Carlsbad, Calif.), and Cambridge antibody Technologies (Cambridgeshire, UK). See, e.g., U.S. Pat. Nos. 4,704,692, 4,939, 666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, U.S. Pat. Nos. 5,427,908, 5,580,717, assigned to Affymax; U.S. Pat. No. 5,885,793, assigned to Cambridge antibody Technologies; U.S. Pat. No. 5,750,373, assigned to Genentech, U.S. Pat. Nos. 5,618,920, 5,595,898, 5,576,195, 5,698,435, 5,693,493, 5,698,417, assigned to Xoma, Colligan, supra; Ausubel, supra; or Sambrook, supra, each of the above patents and publications entirely incorporated herein by reference.

Antibody Fragments

Antibody fragments can be derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. F(ab')2, Fab, Fv and ScFv antibody fragments can all be expressed in and secreted from mammalian host cells or from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')2 fragments (Carter et al., Bio/Technology 10:163-167 (1992)).

In other embodiments, the antibody of is a single chain Fv fragment (scFv). See WO 93/16185; U.S. Pat. No. 5,571, 894; and U.S. Pat. No. 5,587,458. Fv and sFv are species with intact combining sites, that is a VH and VL domain, that are devoid of constant regions. Typically, the VH and VL domains are cloned and re-engineered to lie within a single polypeptide and connected by a flexible linker long enough to allow interaction of the two domains within the single polypeptide. Alternatively, fusion proteins may be constructed to yield fusion of an effector protein at either the amino or the carboxy terminus of an sFv. See Antibody Engineering, 1995. ed. Borrebaeck.

3. Nucleic Acid Molecules

The isolated nucleic acids of the present invention can be made using (a) recombinant methods, (b) synthetic techniques, (c) purification techniques, or combinations thereof, as well-known in the art. DNA encoding the monoclonal antibodies is readily isolated and sequenced using methods known in the art (e.g., by using oligonucleotide probes that are capable of binding specifically to genes encoding the heavy and light chains of murine antibodies). Where a hybridoma is produced, such cells can serve as a source of such DNA. Alternatively, using display techniques such as phage or ribosomal display libraries, the selection of the binder and the nucleic acid is simplified. After phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in International publication No. WO 92/22324; Mullinax et al., 1992, BioTechniques 12(6):864-869; Sawai et al., 1995, AJR134:26-34; and Better et al., 1988, Science 240:1041-1043 (said references entirely incorporated by reference).

Once isolated, the DNA may be placed into expression vectors, which are then transfected into host cells such as E. coli cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Plückthun, Immunol. Revs. 130:151-188 (1992).

Known methods of DNA or RNA amplification include, but are not limited to, polymerase chain reaction (PCR) and related amplification processes. PCR and other in vitro amplification methods can also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, supra, Sambrook, supra, and Ausubel, supra, as well as Mullis, et al., U.S. Pat. No. 4,683,202 (1987); and Innis, et al., PCR Protocols A Guide to Methods and Applications, Eds., Academic Press Inc., San Diego, Calif. (1990). Commercially available kits for genomic PCR amplification are known in the art. See, e.g., Advantage-GC Genomic PCR Kit (Clontech). Additionally, e.g., the T4 gene 32 protein (Boehringer Mannheim) can be used to improve yield of long PCR products.

The isolated nucleic acid compositions of this invention, such as RNA, cDNA, genomic DNA, or any combination thereof, can be obtained from biological sources using any number of cloning methodologies known to those of skill in the art. In some embodiments, oligonucleotide probes that selectively hybridize, under stringent conditions, to the polynucleotides of the present invention are used to identify the desired sequence in a cDNA or genomic DNA library. The isolation of RNA, and construction of cDNA and genomic libraries, is well known to those of ordinary skill in the art. (See, e.g., Ausubel, supra; or Sambrook, supra).

The nucleic acid molecules of the invention are nucleic acids encoding antibodies or antibody portions (e.g., VH, VL, CDR3) that bind to MCP-1. "Isolated nucleic acid molecules" of the invention is intended to refer to a nucleic acid molecule in which the nucleotide sequences encoding the antibody or antibody portion are free of other nucleotide sequences encoding antibodies or antibody portions that bind antigens other than MCP-1. In one embodiment, the anti-human MCP-1 antibody, or portion thereof, includes the nucleotide or amino acid sequence of C775, as well as heavy chain (VH) and light chain (VL) variable regions having the amino acid sequences shown in SEQ ID NOs: 7 and 8, respectively, and nucleotide sequences encoding them, e.g., but not limited to, SEQ ID Nos: 10 and 11 and SEQ ID NOS: 12-17 encoding the individual CDR regions.

Alternatively, in another embodiment, mutations can be introduced randomly along all or part of an anti-MCP-1 antibody coding sequence, such as by saturation mutagenesis or by recombination, and the resulting modified anti-MCP-1 antibodies can be screened for binding activity.

Accordingly, antibodies encoded by the (heavy and light chain variable region) nucleotide sequences disclosed herein (i.e., SEQ ID NOs: 10-11) and/or containing the (heavy and light chain variable region) amino acid sequences disclosed herein (SEQ ID NOs: 7 and 8) include substantially similar antibodies encoded by or containing similar sequences which have been conservatively modified. Further discussion as to how such substantially similar antibodies can be generated based on the partial (i.e., heavy and light chain variable regions) sequences disclosed herein as SEQ ID NOs: 7 and 8 is provided below. For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the sequences hybridize under selective hybridization conditions, to the complement of segments with the strand. The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also determined using the algorithm of E. Meyers and W. Miller (Comput. AppL. Biosci., 4:11-17 (1988)) which has been incorporated into the ALIGN program (version 2.0), using a PAM 1 20 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at http://www.gcg.com), using either a Blossum 62 matrix or a PAM2 5 0 matrix, and a gap weight of 16, 14, 12, 10, 8, 6, or 4 and a length weight of 1, 2, 3, 4, 5, or 6. The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) Nucleic Acids Res. 25(17):3389. When utilizing BLAST and Gapped BLAST programs, the default parameters of the respective programs (e.g., XBLAST and NBLAST) can be used. See http:Hwww.ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof, may be mutated in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

Using the information provided herein, such as nucleotide sequences encoding at least 70-100% of the contiguous amino acids of at least one of SEQ ID NOS: 1, 2, 3, 4, 5, 6, 7, 8, specified fragments, variants or consensus sequences thereof, or a deposited vector comprising at least one of MCP-1 antibody can be obtained using methods described herein or as known in the art.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Coding Sequences

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain or light chain; nucleic acid molecules comprising the coding sequence for an anti-MCP-1 antibody or variable region (e.g., SEQ ID NOS: 7 and 8) including but not limited to SEQ ID Nos; 10 and 11; and nucleic acid molecules which comprise a nucleotide sequence substantially different from those described above but which, due to the degeneracy of the genetic code, still encode at least one anti-MCP-1 antibody as described herein and/or as known in the art. Of course, the genetic code is well known in the art.

Thus, it would be routine for one skilled in the art to generate such degenerate nucleic acid variants that code for specific anti-MCP-1 antibodies of the present invention using alternate codons selections. Such selections can be advantageously applied for generating coding sequences for incorporation into expression vectors encoding the anti-MCP-1 antibodies of the present invention that are compatible with and optimized for expression in diverse host cells from human and nonhuman species.

As indicated herein, nucleic acid molecules of the present invention which comprise a nucleic acid encoding an anti-MCP-1 antibody can include, but are not limited to, those encoding the amino acid sequence of an antibody fragment, by itself; the coding sequence for the entire antibody or a portion thereof; the coding sequence for an antibody, fragment or portion, as well as additional sequences, such as the coding sequence of at least one signal leader or fusion peptide, with or without the aforementioned additional coding sequences, such as at least one intron, together with additional, non-coding sequences, including but not limited to, non-coding 5' and 3' sequences, such as the transcribed, non-translated sequences that play a role in transcription, mRNA processing, including splicing and polyadenylation signals (for example—ribosome binding and stability of mRNA); an additional coding sequence that codes for additional amino acids, such as those that provide additional functionalities. Thus, the sequence encoding an antibody can be fused to a marker sequence, such as a sequence encoding a peptide that facilitates purification of the fused antibody comprising an antibody fragment or portion.

1. Cassettes and Vectors

The invention provides vectors, preferably, expression vectors, containing a nucleic acid encoding the anti-MCP-1 antibody, or may be used to obtain plasmids containing various antibody HC or LC genes or portions thereof. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. The present invention also relates to vectors that include isolated nucleic acid molecules of the present invention, host cells that are genetically engineered with the recombinant vectors, and the production of at least one anti-MCP-1 antibody by recombinant techniques, as is well known in the art. See, e.g., Sambrook, et al., supra; Ausubel, et al., supra, each entirely incorporated herein by reference.

For expression of the antibodies, or antibody fragments thereof, DNAs encoding partial or full-length light and heavy chains, can be inserted into expression cassettes or vectors such that the genes are operatively linked to transcriptional and translational control sequences. A cassette which encodes an antibody, can be assembled as a construct. A construct can be prepared using methods known in the art. The construct can be prepared as part of a larger plasmid. Such preparation allows the cloning and selection of the correct constructions in an efficient manner. The construct can be located between convenient restriction sites on the plasmid or other vector so that they can be easily isolated from the remaining plasmid sequences.

Generally, a plasmid vector is introduced in a precipitate, such as a calcium phosphate precipitate, or in a complex with a charged lipid of DEAE-dextran. If the vector is a virus, it can be packaged in vitro using an appropriate packaging cell line and then transduced into host cells. Introduction of a vector construct into a host cell can also be effected by electroporation or other known methods. Such methods are described in the art, such as Sambrook, supra, Chapters 1-4 and 16-18; Ausubel, supra, Chapters 1, 9, 13, 15, 16.

In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present).

The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VI, segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

In general, a mammalian expression vector will contain (1) regulatory elements, usually in the form of viral promoter or enhancer sequences and characterized by a broad host and tissue range; (2) a "polylinker" sequence, facilitating the insertion of a DNA fragment which comprises the antibody coding sequence within the plasmid vector; and (3) the sequences responsible for intron splicing and polyadenylation of mRNA transcripts. This contiguous region of the promoter-polylinker-polyadenylation site is commonly referred to as the transcription unit. The vector will likely also contain (4) a selectable marker gene(s) (e.g., the beta-lactamase gene), often conferring resistance to an antibiotic (such as ampicillin), allowing selection of initial positive transformants in $E.$ $coli$; and (5) sequences facilitating the replication of the vector in both bacterial and mammalian hosts. A plasmid origin of replication are included for propagation of the expression construct in $E.$ $coli$ and for transient expression in Cos cells, the SV40 origin of replication is included in the expression plasmid.

A promoter may be selected from a SV40 promoter, (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter.

Expression vectors will preferably but optionally include at least one selectable marker. Such markers include, e.g., but not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827, 739) resistance for eukaryotic cell culture, and tetracycline or ampicillin resistance genes for culturing in $E.$ $coli$ and other bacteria or prokaryotics (the above patents are entirely incorporated hereby by reference). Appropriate culture mediums and conditions for the above-described host cells are known in the art. Suitable vectors will be readily apparent to the skilled artisan.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art. Also, to avoid high surface expression of heavy chain molecules, it may be necessary to use an expression vector that eliminates transmembrane domain variant splices.

Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRES1neo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109).

Alternatively, the nucleic acids encoding the antibody sequence can be expressed in stable cell lines that contain the gene integrated into a chromosome. The co-transfection with a selectable marker such as dhfr, gpt, neomycin, or hygromycin allows the identification and isolation of the transfected cells which express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227: 277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

The DNA constructs used in the production of the antibodies of the invention can optionally include at least one insulator sequence. The terms "insulator", "insulator sequence" and "insulator element" are used interchangeably herein. An insulator element is a control element which insulates the transcription of genes placed within its range of action but which does not perturb gene expression, either negatively or positively. Preferably, an insulator sequence is inserted on either side of the DNA sequence to be transcribed. For example, the insulator can be positioned about 200 bp to about 1 kb, 5' from the promoter, and at least about 1 kb to 5 kb from the promoter, at the 3' end of the gene of interest. The distance of the insulator sequence from the promoter and the 3' end of the gene of interest can be determined by those skilled in the art, depending on the relative sizes of the gene of interest, the promoter and the enhancer used in the construct. In addition, more than one insulator sequence can be positioned 5' from the promoter or at the 3' end of the transgene. For example, two or more insulator sequences can be positioned 5' from the promoter. The insulator or insulators at the 3' end of the transgene can be positioned at the 3' end of the gene of interest, or at the 3' end of a 3' regulatory sequence, e.g., a 3' untranslated region (UTR) or a 3' flanking sequence.

Examples of suitable inducible non-fusion E. coli expression vectors include pTrc (Amann et al., (1988) Gene 69:301-315) and pET 11d (Studier et al., Gene Expression Technology: Methods in Enzymology 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS 174(DE3) from a resident λ prophage harboring a T7 gn 1 gene under the transcriptional control of the lacUV 5 promoter.

In another embodiment, the expression vector is a yeast expression vector. Examples of vectors for expression in yeast S. cerevisiae include pYepSec1 (Baldari et al. (1987) EMBO J. 6:229-234), pMFa (Kurjan and Herskowitz, (1982) Cell 30:933-943), pJRY88 (Schultz et al. (1987) Gene 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al. (1983) Mol. Cell Biol. 3:2156-2165) and the pVL series (Lucklow and Summers (1989) Virology 170:31-39).

In yet another embodiment, a nucleic acid of the invention is expressed in mammalian cells using a mammalian expression vector. Examples of mammalian expression vectors include pCDM8 (Seed (1987) Nature 329:840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells, see chapters 16 and 17 of Sambrook et al., supra.

In another embodiment, the recombinant mammalian expression vector is capable of directing expression of the nucleic acid, preferentially in a particular cell type, such as lymphoma cells (e.g., mouse myeloma cells). In specific cell types, tissue-specific regulatory elements are used to express the nucleic acid. Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), in particular, promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873, 316 and European Application Publication No. 264, 166). Developmentally-regulated promoters are also encompassed, for example, by the murine hox promoters (Kessel and Gruss (1990) Science 249:374-379) and the α-fetoprotein promoter (Campes and Tilghman (1989) Genes Dev. 3:537-546).

The invention further provides a recombinant expression vector comprising a DNA molecule cloned into the expression vector in an antisense orientation. That is, the DNA molecule is operably linked to a regulatory sequence in a manner that allows for expression (by transcription of the DNA molecule) of an RNA molecule that is antisense to the mRNA encoding a polypeptide. Regulatory sequences operably linked to a nucleic acid cloned in the antisense orientation can be chosen which direct the continuous expression of the antisense RNA molecule in a variety of cell types. For instance, viral promoters and/or enhancers, or regulatory sequences can be chosen which direct constitutive, tissue specific, or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes, see Weintraub et al. (Reviews—Trends in Genetics, Vol. 1(1) 1986).

Cloning and Expression in Myeloma Cells

A chimeric mouse/human IgG1k monoclonal antibody against human CD4, known as cM-T412 (EP0511308 entirely incorporated by reference), was observed to be expressed at high levels in transfected mouse myeloma cells (Looney et al. 1992. Hum Antibodies Hybridomas 3(4):191-200). Without a large effort at optimizing culture conditions, production levels of >500 mg/L (specific productivity on a pg/cell/day basis not known) were readily obtained at Centocor, Inc. Malvern, Pa. in 1990. Based on the components of these expression vectors antibody-cloning vectors were developed useful for HC and LC cloning which include the gene promoter/transcription initiation nucleic acid sequence, the 5' untranslated sequences and translation initiation nucleic acid sequences, the nucleic acid sequences encoding the signal sequence, the intron/exon splice donor sequences for the signal intron and the J-C intron, and the J-C intron enhancer nucleic acid sequences. Plasmid p139, a pUC19 plasmid, contains a 5.8 kb EcoRI-EcoRI genomic fragment cloned from C123 hybridoma cells secreting the fully mouse M-T412 Ab; the fragment contains the promoter and V region part of the cM-T412 HC gene. The starting material for LC V region vector engineering was plasmid p39, a pUC plasmid that contains a 3 kb HindIII-HindIII genomic fragment cloned from C123 hybridoma cells; this fragment contains the promoter and V region part of the cM-T412 LC gene. The engineered vectors derived from p139 and p39 were designed to enable convenient assembly of HC or LC genes suitable for expression in a mammalian host cell in a two-step process that entails 1) cloning DNA encoding a sequence of interest between specially-prepared restriction sites in a V region vector, whereby the V-region coding sequence is positioned immediately downstream of the vector-encoded signal sequence, as well as downstream of part or all of the gene promoter; and 2) transferring a fragment that spans the inserted sequence from the V region vector to the C region vector in the proper orientation whereby the resulting plasmid constitutes the final expression plasmid suitable for expression in cells (Scallon et al. 1995 Cytokine 7(8):759-769).

Cloning and Expression in CHO Cells

Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (e.g., alpha minus MEM, Life Technologies, Gaithersburg, Md.) supplemented with the chemotherapeutic agent methotrexate.

The amplification of the DHFR genes in cells resistant to methotrexate (MTX) has been well documented (see, e.g., F. W. Alt, et al., J. Biol. Chem. 253:1357-1370 (1978); J. L. Hamlin and C. Ma, Biochem. et Biophys. Acta 1097:107-143 (1990); and M. J. Page and M. A. Sydenham, Biotechnology 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach can be used to develop cell lines carrying more than 1,000 copies of the amplified gene(s). Subsequently, when the methotrexate is withdrawn, cell lines are obtained that contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., Molec. Cell. Biol. 5:438-447 (1985)) plus a fragment isolated from the enhancer of the immediate early gene of human cytomegalovirus (CMV) (Boshart, et al., Cell 41:521-530 (1985)). Downstream of the promoter are BamHI, XbaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human b-actin promoter, the SV40 early or late promoters or the long terminal repeats from other retroviruses, e.g., HIV and HTLVI. Clontech's Tet-Off and Tet-On gene expression systems and similar systems can be used to express the MCP-1 antibody in a regulated way in mammalian cells (M. Gossen, and H. Bujard, Proc. Natl. Acad. Sci. USA 89: 5547-5551 (1992)). For the polyadenylation of the mRNA other signals, e.g., from the human growth hormone or globin genes can be used as well.

5. Host Cells for Production of Antibodies

Unlike most genes that are transcribed from continuous genomic DNA sequences, antibody genes are assembled from gene segments that may be widely separated in the germ line.

In particular, heavy chain genes are formed by recombination of three genomic segments encoding the variable (V), diversity (D) and joining (J)/constant (C) regions of the antibody. Functional light chain genes are formed by joining two gene segments; one encodes the V region and the other encodes the J/C region. Both the heavy chain and kappa light chain loci contain many V gene segments (estimates vary between 100s and 1000s) estimated to span well over 1000 kb. The lambda locus is, by contrast, much smaller and has been shown to span approximately 300 kb on chromosome 16 in the mouse. It consists of two variable gene segments and four joining/constant (J/C) region gene segments. Formation of a functional gene requires recombination between a V and a J/C element.

In the B-cell in which the antibody is naturally produced, control of transcription of both rearranged heavy and kappa light chain genes depends both on the activity of a tissue specific promoter upstream of the V region and a tissue specific enhancer located in the J-C intron. These elements act synergistically. Also, a second B-cell specific enhancer has been identified in the kappa light chain locus. This further enhancer is located 9 kb downstream of $C_{kappa}$. Thus, the hybridoma method of immortalizing antibody expression genes relies on the endogenous promoter and enhancer sequences of the parent B-cell lineage. Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Cloning of antibody genomic DNA into an artificial vector is another method of creating host cells capable of expressing antibodies. However, expression of monoclonal antibodies behind a strong promoter increases the chances of identifying high-producing cell lines and obtaining higher yields of monoclonal antibodies. Antibodies of the invention can be produced in a host cell transfectoma using, for example, a combination of recombinant DNA techniques and gene transfection methods as is well known in the art (e.g., Morrison, S. (1985) Science 229:1202).

Systems for cloning and expression of a polypeptide in a variety of different host cells are well known. Suitable host cells include bacteria, mammalian cells, plant cells, yeast and baculovirus systems and transgenic plants and animals.

Mammalian cell lines available in the art for expression of a heterologous polypeptide intact glycosylated proteins include Chinese hamster ovary (CHO) cells, HeLa cells, baby hamster kidney cells (BHK), NSO mouse melanoma cells and derived cell lines, e.g. SP2/0, YB2/0 (ATC CRL-1662) rat myeloma cells, human embryonic kidney cells (HEK), human embryonic retina cells PerC.6 cells, hep G2 cells, BSC-1 (e.g., ATCC CRL-26) and many others available from, for example, American Type Culture Collection, Manassas, Va. (www.atcc.org). A common, preferred bacterial host is E. coli.

Mammalian cells such as CHO cells, myeloma cells, HEK293 cells, BHK cells (BHK21, ATCC CRL-10), mouse Ltk-cells, and NIH3T3 cells have been frequently used for stable expression of heterologous genes. In contrast, cell lines such as Cos (COS-1 ATCC CRL 1650; COS-7, ATCC CRL-1651) and HEK293 are routinely used for transient expression of recombinant proteins.

Preferred mammalian host cells for expressing the recombinant antibodies of the invention include myeloma cells such as Sp2/0, YB2/0 (ATC CRL-1662), NSO, and P3X63.Ag8.653 (e.g. SP2/0-Ag14) because of their high rate of expression. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Illustrative of cell cultures useful for the production of the antibodies, specified portions or variants thereof, are mammalian cells. Mammalian cell systems often will be in the form of monolayers of cells although mammalian cell suspensions or bioreactors can also be used.

CHO-K1 and DHFR–CHO cells DG44 and DUK-B11 (G. Urlaub, L. A. Chasin, 1980. Proc. Natl. Acad. Sci. U.S.A. 77, 4216-4220) are used for high-level protein production because the amplification of genes of interest is enabled by the incorporation of a selectable, amplifiable marker, DHFR using e.g. the drug methotrexate (MTX) (R. J. Kaufman, 1990. Methods Enzymol. 185: 537-566). DHFR$^-$ CHO cells can be successfully used to produce recombinant mAbs at a high level. DHFR$^-$ CHO may produce ant-MCP-1 antibodies at the rate of 80-110 mg $10^6$ cells$^{-1}$ day$^{-1}$ or more than 200 mg $10^6$ cells$^{-1}$ day$^{-1}$. A variety of promoters have been used to obtain expression of H- and L-chains in these CHO cells, for example, the b-actin promoter, the human CMV MIE promoter, the Ad virus major late promoter (MLP), the RSV promoter, and a murine leukemia virus LTR. A number of vectors for mAb expression are described in the literature in which the two Ig chains are carried by two different plasmids with an independent selectable/amplifiable marker. Vectors containing one antibody chain, e.g. the H-chain, linked to a DHFR marker, and an L-chain expression cassette with the Neo$^r$ marker or vice versa to can be used obtain up to 180 mg of a humanized mAb L$^{-1}$ 7 day$^{-1}$ in spinner flasks. The methods used for initial selection and subsequent amplification can be varied and are well known to those skilled in the art. In general, high-level mAb expression can be obtained using the following steps: initial selection and subsequent amplification of candidate clones, coselection (e.g., in cases where both H-chain and L-chain expression vectors carry DHFR expression unit) and amplification, coamplification using different amplifiable markers, and initial selection and amplification in mass culture, followed by dilution cloning to identify individual high-expressing clones. Because integration sites may influence the efficiency of H-chain and L-chain expression and overall mAb expression, single vectors have been created in which the two Ig-chain expression units are placed in tandem. These vectors also carry a dominant selectable marker such as Neo$^r$ and the DHFR expression cassette. For a review see Ganguly, S. and A. Shatzman. Expression Systems, mammalian cells IN: Encyclopedia of Bioprocess Technology: Fermentation, Biocatalysis, and Bioseparation. 1999 by John Wiley & Sons, Inc.

Cockett et al. (1990. Bio/Technology 8, 662-667) developed the GS system for high-level expression of heterologous genes in CHO cells. Transfection of an expression vector containing a cDNA (under the transcriptional control of the hCMV promoter) and a GS mini gene (under the control of the SV40 late promoter) into CHO-K1 cells (followed by selection with 20 mM to 500 mM MSX) can be used to yield clones expressing the antibodies of the invention in yields comparable to that of the DHFR– CHO systems. The GS system is discussed in whole or part in connection with European Patent Nos. 0 216 846, 0 256 055, and 0 323 997 and European Patent Application No. 89303964.4.

6. Alternative Methods of Producing Antibodies

Where antibody fragments are desired, such antibody fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the CH$_1$ domain and/or hinge region of the heavy chain. The various portions of antibodies can be joined together chemically by conventional techniques, or can be prepared as a contiguous protein using genetic engineering techniques.

In an alternative method of producing the antibodies of the invention, a non-human animal in which is one or more, and preferably essentially all, of the cells of the animal contain a heterologous nucleic acid introduced by way of human intervention, a transgene, coding for the antibody. The transgene can be introduced into the cell, directly or indirectly, by introduction into a precursor of the cell, by way of deliberate genetic manipulation, such as by microinjection or by infection with a recombinant virus. Methods for generating non-human transgenic mammals are known in the art. See, e.g., but not limited to, U.S. Pat. Nos. 5,827,690; 5,849,992; 4,873,316; 5,849,992; 5,994,616; 5,565,362; 5,304,489, and the like, each of which is entirely incorporated herein by reference. Such methods can involve introducing DNA constructs into the germ line of a mammal to make a transgenic mammal. For example, one or several copies of the construct may be incorporated into the genome of a mammalian embryo by standard transgenic techniques. In addition, non-human transgenic mammals can be produced using a somatic cell as a donor cell. The genome of the somatic cell can then be inserted into an oocyte and the oocyte can be fused and activated to form a reconstructed embryo. For example, methods of producing transgenic animals using a somatic cell are described in PCT Publication WO 97/07669; Baguisi et al. NATURE BIOTECH., vol. 17 (1999), 456-461; Campbell et al., NATURE, vol. 380 (1996), 64-66; Cibelli et al., SCIENCE, vol. 280 (1998); Kato et al., SCIENCE, vol. 282 (1998), 2095-2098; Schnieke et al., SCIENCE, vol. 278. (1997), 2130-2133; Wakayama et al., NATURE, vol. 394 (1998), 369-374; Well et al., BIOL. REPROD., vol. 57 (1997):385-393.

It is desirable to express a heterologous protein, e.g., an antibody, in a specific tissue or fluid, e.g., the milk, of a transgenic animal. The heterologous protein can be recovered from the tissue or fluid in which it is expressed. For example, the antibodies of the present invention can be expressed in the milk of a transgenic animal. Methods for producing a heterologous protein under the control of a mammary gland specific promoter are known. For mammary gland expression, useful transcriptional promoters are those promoters that are preferentially activated in mammary epithelial cells, including promoters that control the genes encoding milk proteins such as caseins, beta lactoglobulin (Clark et al., (1989) BIO/TECHNOLOGY 7: 487-492), whey acid protein (Gordon et al. (1987) BIO/TECHNOLOGY 5: 1183-1187), and lactalbumin (Soulier et al., (1992) FEBS Letts. 297: 13). Casein promoters may be derived from the alpha, beta, gamma or kappa casein genes of any mammalian species; a preferred promoter is derived from the goat beta casein gene (DiTullio, (1992) BIO/TECHNOLOGY 10:74-77). The promoter can also be from lactoferrin or butyrophin.

Antibodies of the present invention can additionally be produced using at least one anti-MCP-1 antibody encoding nucleic acid to provide transgenic plants and cultured plant cells (e.g., but not limited to tobacco, maize, and duckweed) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbiol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and reference cited therein. Thus, antibodies of the present invention can also be produced using transgenic plants, according to know methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109: 341-6 (1995); Whitelam et al., Biochem. Soc. Trans. 22:940-944 (1994); and references cited therein. See, also generally for plant expression of antibodies, but not limited to, each of the above references is entirely incorporated herein by reference.

7. Synthetic Methods for Constructing Nucleic Acids

The isolated nucleic acids of the present invention can also be prepared by direct chemical synthesis by known methods (see, e.g., Ausubel, et al., supra). Chemical synthesis generally produces a single-stranded oligonucleotide, which can be converted into double-stranded DNA by hybridization with a complementary sequence, or by polymerization with a DNA polymerase using the single strand as a template. One of skill in the art will recognize that while chemical synthesis of DNA can be limited to sequences of about 100 or more bases, longer sequences can be obtained by the ligation of shorter sequences. Such methods are taught in, for example; U.S. Pat. No. 5,942,609, U.S. Pat. No. 6,521,427, U.S. Pat. No. 6,586,211, or U.S. Pat. No. 6,670,127.

8. Purification of an Antibody

An anti-MCP-1 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography such as with a Protein A column, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

9. Anti-MCP-1 Antibody Compositions

The present invention also provides at least one anti-MCP-1 antibody composition comprising at least one, at least two, at least three, at least four, at least five, at least six or more anti-MCP-1 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the antiMCP-1 antibody amino acid sequence selected from the group consisting of 70-100% of the contiguous amino acids of SEQ ID NOS: 1, 2, 3, 4, 5, 6, 7, 8, or specified fragments, domains or variants thereof. Preferred anti-MCP-1 antibody compositions include at least one or two full length, fragments, domains or variants as at least one CDR or LBR containing portions of the anti-MCP-1 antibody sequence of 70-100% of SEQ ID NOS:1, 2, 3, 4, 5, 6, or specified fragments, domains or variants thereof. Further preferred compositions comprise 40-99% of at least one of 70-100% of SEQ ID NOS: 1, 2, 3, 4, 5, 6, or specified fragments, domains or variants thereof. Such composition percentages are by weight, volume, concentration, molarity, or molality as liquid or dry solutions, mixtures, suspension, emulsions or colloids, as known in the art or as described herein.

Fusion Proteins

At least one antibody of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. To assist in affinity purification, various tag polypeptides and their respective antibodies are well known in the art. Examples include poly-histidine (poly-his) or poly-histidine-glycine (poly-his-gly) tags; the flu HA tag polypeptide and its antibody 12CA5 (Field et al., Mol. Cell. Biol, 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Enoineering 3(6):547-553 (1990)). Other tag polypeptides include the Flag-peptide (Hopp et al., Bio Technology, 6:1204-1210 (1988)); the KT3 epitope peptide (Martin et al., Science, 255:192-194 (1992)); an .alpha.-tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87:6393-6397 (1990)). A preferred tag is the FLAG tag.

Antibody Conjugates

In another aspect, the invention relates to antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate ($C_{12}$, laurate), n-tetradecanoate ($C_{14}$, myristate), n-octadecanoate ($C_{18}$, stearate), n-eicosanoate ($C_{20}$, arachidate), n-docosanoate ($C_{22}$, behenate), n-triacontanoate ($C_{30}$), n-tetracontanoate ($C_{40}$), cis-$\Delta$9-octadecanoate ($C_{18}$, oleate), all cis-$\Delta$5,8,11,14-eicosatetraenoate ($C_{20}$, arachidonate), octanedioic acid, tetradecanedioic acid, octadecanedioic acid, docosanedioic acid, and the like. Suitable fatty acid esters include mono-sters of dicarboxylic acids that comprise a linear or branched lower alkyl group. The lower alkyl group can comprise from one to about twelve, preferably one to about six, carbon atoms.

The modified antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent $C_1$-$C_{12}$ group wherein one or more carbon atoms can be replaced by a heteroatom such as oxygen, nitrogen or sulfur. Suitable linker moieties include, for example, tetraethylene glycol, —$(CH_2)_3$—, —NH—$(CH_2)_6$—NH—, —$(CH_2)_2$—NH— and —$CH_2$—O—$CH_2$—$CH_2$—O—$CH_2$—$CH_2$—O—CH—NH—. Modifying agents that comprise a linker moiety can be produced, for example, by reacting a mono-Boc-alkyldiamine (e.g., mono-Boc-ethylenediamine, mono-Bocdiaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO92/16221 the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

10. Anti-Idiotype Antibodies to Anti-MCP-1 Antibody

In addition to monoclonal or chimeric anti-MCP-1 antibodies, the present invention is also directed to an anti-idiotypic (anti-Id) antibody specific for such antibodies of the invention. An anti-Id antibody is an antibody that recognizes unique determinants generally associated with the antigen-binding region of another antibody. The anti-Id can be prepared by immunizing an animal of the same species and genetic type (e.g. mouse strain) as the source of the Id antibody with the antibody or a CDR containing region thereof. The immunized animal will recognize and respond to the idiotypic determinants of the immunizing antibody and produce an anti-Id antibody. The anti-Id antibody may also be used as an "immunogen" to induce an immune response in yet another animal, producing a so-called anti-anti-Id antibody.

11. Anti-MCP-1 Antibody Pharmaceutical Compositions

Anti-MCP-1 antibody compositions of the present invention can further comprise at least one of any suitable and effective amount of a composition or pharmaceutical composition comprising at least one anti-MCP-1 antibody to a cell, tissue, organ, animal or patient in need of such modulation, treatment or therapy, optionally further comprising at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteroid, (dexamethasone), an anabolic steroid (testosterone), a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin (rituximab), an immunosuppressive (e.g., basiliximab, cyclosporine, daclizumab), a growth hormone, a hormone antagonist, a reproductive hormone antagonist (flutamide, nilutamide), a hormone release modulator (leuprolide, goserelin), a hormone replacement drug, an estrogen receptor modulator (tamoxifen), a retinoid (tretinoin), a topoisomerase inhibitor (etoposide, irinotecan), a cytotoxin (doxorubicin, dacarbazine), a mydriatic, a cycloplegic, an alkylating agent (carboplatin), a nitrogen mustard (melphalen, chlorabucil), a nitrosourea (carmustine, estramustine) an antimetabolite (methotrexate, cytarabine, fluorouracil), a mitotic inhibitor (vincristine, taxol), a radiopharmaceutical (Iodine 131-tositumomab), a radiosensitizer (misonidazole, tirapazamine) an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine (interferon alpha-2, IL2) or a cytokine antagonist (infliximab). Non-limiting examples of such cytokines include, but are not limted to, any of IL-1 to IL-23, IL-6, anti-tumor antibodies, chemotherapeutic agents or radiation therapies. Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer compositions can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:

H7), Staphylococcus species (e.g., Staphylococcus aureus, Staphylococcus pyogenes), Shigella species (e.g., Shigella dysenteriae, Shigella flexneri, Shigella boydii, and Shigella sonnei), Salmonella species (e.g., Salmonella typhi, Salmonella cholera-suis, Salmonella enteritidis), Clostridium species (e.g., Clostridium perfringens, Clostridium dificile, Clostridium botulinum), Camphlobacter species (e.g., Camphlobacter jejuni, Camphlobacter fetus), Heliobacter species, (e.g., Heliobacter pylori), Aeromonas species (e.g., Aeromonas sobria, Aeromonas hydrophila, Aeromonas caviae), Pleisomonas shigelloides, Yersina enterocolitica, Vibrios species (e.g., Vibrios cholerae, Vibrios parahemolyticus), Klebsiella species, Pseudomonas aeruginosa, and Streptococci. See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, New York (1990); Berkow et al, eds., The Merck Manual, 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

Anti-MCP-1 antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18$^{th}$ Edition, Mack Publishing Co. (Easton, Pa.) 1990. Pharmaceutically acceptable carriers can be routinely selected that are suitable for the mode of administration, solubility and/or stability of the anti-MCP-1 antibody, fragment or variant composition as well known in the art or as described herein.

12. Formulations

As noted above, the invention provides for stable formulations, which preferably contain buffering components and, optionally, stabilizers or preservatives, as well as multi-use formulations suitable for pharmaceutical or veterinary use, comprising at least one anti-MCP-1 antibody in a pharmaceutically acceptable formulation.

Anti-MCP-1 antibody compositions may include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are amino acids or organic acid salts such as citrate. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8.

Other additives, such as a pharmaceutically acceptable solubilizers such as surfactants: Tween 20 (polyoxyethylene (20) sorbitan monolaurate), Tween 40 (polyoxyethylene (20) sorbitan monopalmitate), Tween 80 (polyoxyethylene (20) sorbitan monooleate); Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA can optionally be added to the formulations or compositions to reduce aggregation. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein such as MCP-1 antibodies, or specified portions or variants, can also be included in the formulation.

These additives are particularly useful if a pump or plastic container is used to administer the formulation. The presence of pharmaceutically acceptable surfactant mitigates the propensity for the protein to aggregate.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, protamine and the like.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol, aldonic acids, such as gluconate, esterified sugars, and the like. Preferred carbohydrate excipients for use in the present invention are mannitol, trehalose, and raffinose.

Additionally, anti-MCP-1 antibody compositions of the invention can include polymeric excipients/additives such as polyvinylpyrrolidones, ficolls (a polymeric sugar), dextrates (e.g., cyclodextrins, such as 2-hydroxypropyl-alpha-cyclodextrin), polyethylene glycols, flavoring agents, antimicrobial agents, sweeteners, antioxidants, antistatic agents, lipids (e.g., phospholipids, fatty acids), steroids (e.g., cholesterol), and chelating agents (e.g., EDTA).

These and additional known pharmaceutical excipients and/or additives suitable for use in the anti-MCP-1 antibody, portion or variant compositions according to the invention are known in the art, e.g., as listed in "Remington: The Science & Practice of Pharmacy", 19$^{th}$ ed., Williams & Williams, (1995), and in the "Physician's Desk Reference", 52$^{nd}$ ed., Medical Economics, Montvale, N.J. (1998), Bontempo. 2005 "Parenteral Formulation for Peptides, Proteins, and Monoclonal Antibodies Drugs: A Commercial Development Overview" Drug Delivery. Editor(s): B. Wang, T J. Siahaan, R. Soltero. John Wiley & Sons, Inc. p 321-339; the disclosures of which are entirely incorporated herein by reference.

Preparation

The formulations of the present invention can be prepared by a process which comprises mixing at least one anti-MCP-1 antibody and an aqueous diluent. The diluent will preferable contain buffering components and, optionally, stabilizers or preservatives. Mixing the at least one anti-MCP-1 antibody in an aqueous diluent is carried out using conventional dissolution and mixing procedures. Variations of this process would be recognized by one of ordinary skill in the art. For example, the order the components are added, whether additional additives are used, the temperature and pH at which the formulation is prepared, are all factors that can be optimized for the concentration and means of administration used.

At least one anti-MCP-1 antibody in either the stable or preserved formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art. The formulation is sterilized by known or suitable techniques.

Parenteral Administration

Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

Alternative Delivery

The invention further relates to the administration of at least one anti-MCP-1 antibody by parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means.

Many known and developed modes of can be used according to the present invention for administering pharmaceutically effective amounts of at least one anti-MCP-1 antibody according to the present invention. MCP-1 antibodies of the present invention can be delivered in a carrier, as a solution, emulsion, colloid, or suspension, or as a dry powder, using any of a variety of devices and methods suitable for administration by inhalation or other modes described here within or known in the art.

Pulmonary/Nasal Administration

For pulmonary administration, preferably at least one anti-MCP-1 antibody composition is delivered in a particle size effective for reaching the lower airways of the lung or sinuses. According to the invention, at least one anti-MCP-1 antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use of formulations suitable for the administration for the dispensing of antibody in an aerosol. Such aerosols can be comprised of either solutions (both aqueous and non aqueous) or solid particles. Metered dose inhalers like the Ventolin® metered dose inhaler, typically use a propellant gas and require actuation during inspiration (See, e.g., WO 94/16970, WO 98/35888). Dry powder inhalers like Turbuhaler™ (Astra), Rotahaler® (Glaxo), Diskus® (Glaxo), Spiros™ inhaler (Dura), devices marketed by Inhale Therapeutics, and the Spinhaler® powder inhaler (Fisons), use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like AERx™ Aradigm, the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one anti-MCP-1 antibody is delivered by a dry powder inhaler or a sprayer. There are a several desirable features of an inhalation device for administering at least one antibody of the present invention. For example, delivery by the inhalation device is advantageously reliable, reproducible, and accurate. The inhalation device can optionally deliver small dry particles, e.g. less than about 10 micron, preferably about 1-5 micron, for good respirability.

Oral Formulations and Administration

Formulations for oral delivery of proteins must take into account the process of digestion that degrade polypeptides, namely acid hydrolysis and proteolytic cleavage. Therefore, encapsulated froms of the protein may be useful. These dosage forms can also contain other type(s) of additives, e.g., inactive diluting agent, lubricant such as magnesium stearate, paraben, preserving agent such as sorbic acid, ascorbic acid, alpha.-tocopherol, antioxidant such as cysteine, disintegrator, binder, thickener, buffering agent, sweetening agent, flavoring agent, perfuming agent, etc.

More recently, microspheres of artificial polymers of mixed amino acids (proteinoids) have been used to deliver pharmaceuticals (U.S. Pat. No. 4,925,673). Furthermore, carrier compounds described in U.S. Pat. No. 5,879,681 and U.S. Pat. No. 5,5,871,753 are used to deliver biologically active agents orally are known in the art.

Mucosal Formulations and Administration

For absorption through mucosal surfaces, compositions and methods of administering at least one anti-MCP-1 antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

Prolonged Administration and Formulations

It can be sometimes desirable to deliver the compounds of the present invention to the subject over prolonged periods of time, for example, for periods of one week to one year from a single administration. Various slow release, depot or implant dosage forms can be utilized. For example, a dosage form can contain a pharmaceutically acceptable slow release, depot or implant formulations, (Kost et al. "Drug Delivery Systems", In: Kirk-Othmer Encyclopedia of Chemical Technology, 2004 by John Wiley & Sons, Inc.).

For prolonged delivery or sustained-release, the at least one anti-MCP-1 antibody is encapsulated in a delivery structure such as a liposome or polymeric nanoparticles, microparticle, microcapsule, or microspheres (referred to collectively as microparticles unless otherwise stated). A number of suitable structures are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

For transdermal delivery the anti-MCP-1 antibody may be incorporated in to therapeutic bandage or transdermal patch to be placed in contact with the skin for passive uptake into the body of the subject (see e.g. U.S. Pat. Nos. 3,742,951; 3,797,494; 4,834,979). Alternatively, the anti-MCP-1 antibody in a suitable formulation may be loaded into a mechanical device and delivered by the force of e.g. a peristaltic pump or by iontophorectic force (see e.g. U.S. Pat. Nos. 5,288,289; 5,811,465, 6,756,052).

13. Articles of Manufacture

As noted above, the invention provides an article of manufacture, comprising packaging material and at least one vial comprising a solution of at least one anti-MCP-1 antibody with the prescribed buffers and/or preservatives, optionally in an aqueous diluent, wherein said packaging material comprises a label that indicates that such solution can be held over a period of time, e.g. 72 hours or greater. The invention further comprises an article of manufacture, comprising packaging material, a first vial comprising lyophilized at least one anti-MCP-1 antibody, and a second vial comprising an aqueous diluent of prescribed buffer or preservative, wherein said packaging material comprises a label that instructs a health care professional or a patient to reconstitute the at least one anti-MCP-1 antibody in the aqueous diluent to form a solution that can be held over a period of twenty-four hours or greater. Either a single solution vial or dual vial requiring reconstitution can be reused multiple times and can suffice for a single or multiple cycles of patient treatment and thus can provide a more convenient treatment regimen than currently available.

The aqueous diluent typically comprises a pharmaceutically acceptable buffer such as sodium citrate, L-histidine and L-histidine hydrochloride monohydrate, sodium phosphate in sterile water for injection and adjusted to a suitable pH. Preferably, the aqueous diluent optionally further comprises a pharmaceutically acceptable polypeptide stabilizer. Polypeptide stabilizers include sucrose, sodium chloride, L-arginine, and polysorbate 20, polysorbate 80, and (alpha)-trehalose dehydrate. The aqueous diluent optionally further comprises a pharmaceutically acceptable preservative. Preferred preservatives include those selected from the group consisting of benzyl alcohol, benzalkonium chloride, benzethonium chloride, sodium dehydroacetate, or mixtures thereof. The concentrations are dependent on the diluent buffer, if any, the stabilizer and the preservative selected and are readily determined by the skilled artisan.

The range of at least one anti-MCP-1 antibody in the product of the present invention includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2 to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The claimed products can be provided indirectly to patients by providing to pharmacies, clinics, or other such institutions and facilities, clear solutions or dual vials comprising a vial of lyophilized at least one anti-MCP-1 antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens®, BD Autojector®, Humaject®, NovoPen®, B-D®Pen, AutoPen®, and OptiPen®, GenotropinPen®, Genotronorm Pen®, Humatro Pen®, Reco-Pen®, Roferon Pen®, Biojector®, iject®, J-tip Needle-Free Injector®, Intraject®, Medi-Ject®, e.g., as made or developed by Becton Dickensen® (Franklin Lakes, N.J., www.bectondickenson.com), Disetronic® (Burgdorf, Switzerland, www.disetronic.com); Bioject®, Portland, Oreg. (www.bioject.com); National Medical Products®, Weston Medical® (Peterborough, UK, www.weston-medical.com), Medi-Ject Corp® (Minneapolis, Minn., www.mediject.com). Recognized devices comprising a dual vial system include those pen-injector systems for reconstituting a lyophilized drug in a cartridge for delivery of the reconstituted solution such as the HumatroPen®.

14. Therapeutic Applications

The anti-MCP-1 antibodies of the present invention or specified variants thereof can be used to measure or effect in an cell, tissue, organ or animal (including mammals and humans), to diagnose, monitor, modulate, treat, alleviate, help prevent the incidence of, or reduce the symptoms of, at least one condition mediated, affected or modulated by MCP-1. Such conditions are selected from, but not limited to, diseases or conditions mediated by cell adhesion and/or angiogenesis. Such diseases or conditions include an immune disorder or disease, a cardiovascular disorder or disease, an infectious, malignant, and/or neurologic disorder or disease, or other known or specified MCP-1 related conditions. In particular, the antibodies are useful for the treatment of diseases that involve angiogenesis such as disease of the eye and neoplastic disease, tissue remodeling such as restenosis, and proliferation of certain cells types particularly epithelial and squamous cell carcinomas. Particular indications include use in the treatment of atherosclerosis, restenosis, cancer metastasis, rheumatoid arthritis, diabetic retinopathy and macular degeneration. The neutralizing antibodies of the invention are also useful to prevent or treat unwanted bone resorption or degradation, for example as found in osteoporosis or resulting from PTHrP overexpression by some tumors. The antibodies may also be useful in the treatment of various fibrotic diseases such as idiopathic pulmonary fibrosis, diabetic nephropathy, hepatitis, and cirrhosis.

Thus, the present invention provides a method for modulating or treating at least one MCP-1 related disease, in a cell, tissue, organ, animal, or patient, as known in the art or as described herein, using at least one MCP-1 antibody of the present invention. Particular indications are discussed below:

Pulmonary Disease

The present invention also provides a method for modulating or treating at least one malignant disease in a cell, tissue, organ, animal or patient, including, but not limited to, at least one of: pneumonia; lung abscess; occupational lung diseases caused be agents in the form or dusts, gases, or mists; asthma, bronchiolitis fibrosa obliterans, respiratory failure, hypersensitivity diseases of the lungs includeing hypersensitivity pneumonitis (extrinsic allergic alveolitis), allergic bronchopulmonary aspergillosis, and drug reactions; adult respiratory distress syndrome (ARDS), Goodpasture's Syndrome, chronic obstructive airway disorders (COPD), idiopathic interstitial lung diseases such as idiopathic pulmonary fibrosis and sarcoidosis, desquamative interstitial pneumonia, acute interstitial pneumonia, respiratory bronchiolitis-associated interstitial lung disease, idiopathic bronchiolitis obliterans with organizing pneumonia, lymphocytic interstitial pneumonitis, Langerhans' cell granulomatosis, idiopathic pulmonary hemosiderosis; acute bronchitis, pulmonary alveolar proteinosis, bronchiectasis, pleural disorders, atelectasis, cystic fibrosis, and tumors of the lung, and pulmonary embolism.

Malignant Disease

The present invention also provides a method for modulating or treating at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, pancreatic carcinoma, renal cell carcinoma, breast cancer, nasopharyngeal carcinoma, malignant histiocytosis, paraneoplastic syndrome/ hypercalcemia of malignancy, solid tumors, adenocarcinomas, squamous cell carcinomas, sarcomas, malignant melanoma, particularly metastatic melanoma, hemangioma, metastatic disease, cancer related bone resorption, cancer related bone pain, and the like.

Immune Related Disease

The present invention also provides a method for modulating or treating at least one immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic iupus erythematosis, antiphospholipid syndrome, iridocyclitis/uveitis/ optic neuritis, idiopathic pulmonary fibrosis, systemic vasculitis/wegener's granulomatosis, sarcoidosis, orchitis/ vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitity reactions, allergic rhinitis, hay fever, perennial rhinitis, conjunctivitis, endometriosis, asthma, urticaria, systemic anaphalaxis, dermatitis, pernicious anemia, hemolytic disesease, thrombocytopenia, graft rejection of any organ or tissue, kidney translplant rejection, heart transplant rejection, liver transplant rejection, pancreas transplant rejection, lung transplant rejection, bone marrow transplant (BMT) rejection, skin allograft rejection, cartilage transplant rejection, bone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, OKT3 therapy, anti-CD3 therapy, cytokine therapy, chemotherapy, radiation therapy (e.g., including but not limited toasthenia, anemia, cachexia, and the like), chronic salicylate intoxication, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

Cardiovascular Disease

The present invention also provides a method for modulating or treating at least one cardiovascular disease in a cell, tissue, organ, animal, or patient, including, but not limited to, at least one of cardiac stun syndrome, myocardial infarction, congestive heart failure, stroke, ischemic stroke, hemorrhage, arteriosclerosis, atherosclerosis, restenosis, diabetic ateriosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrythmias, ventricular fibrillation, His bundle arrythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneuryisms, aortic dissection, inflammation of the aorta, occulsion of the abdominal aorta and its branches, peripheral vascular disorders, occulsive arterial disorders, peripheral atherlosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like. Such a method can optionally comprise administering an effective amount of a composition or pharmaceutical composition comprising at least one anti-MCP-1 antibody to a cell, tissue, organ, animal or patient in need of such modulation, treatment or therapy.

Neurologic Disease

The present invention also provides a method for modulating or treating at least one neurologic disease in a cell, tissue, organ, animal or patient, including, but not limited to, at least one of: neurodegenerative diseases, multiple sclerosis, migraine headache, AIDS dementia complex, demyelinating diseases, such as multiple sclerosis and acute transverse myelitis; extrapyramidal and cerebellar disorders' such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multi.system disorder); demyelinating core disorders, such as multiple sclerosis, acute transverse myelitis; and disorders of the motor unit' such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like. Such a method can optionally comprise administering an effective amount of a composition or pharmaceutical composition comprising at least one TNF antibody or specified portion or variant to a cell, tissue, organ, animal or patient in need of such modulation, treatment or therapy. See, e.g., the Merck Manual, 16$^{th}$ Edition, Merck & Company, Rahway, N.J. (1992).

Other Therapeutic Uses of Anti-MCP-1 Antibodies

In addition to the above described conditions and diseases, the present invention also provides a method for modulating or treating fibrotic conditions of various etiologies such as liver fibrosis (including but not limited to alcohol-induced cirrhosis, viral-induced cirrhosis, autoimmune-induced hepatitis); lung fibrosis (including but not limited to scleroderma, idiopathic pulmonary fibrosis); kidney fibrosis (including but not limited to scleroderma, diabetic nephritis, glomerular pehpritis, lupus nephritis); dermal fibrosis (including but not limited to scleroderma, hypertrophic and keloid scarring, burns); myelofibrosis; Neurofibromatosis; fibroma; intestinal fibrosis; and fibrotic adhesions resulting from surgical procedures.

The present invention also provides a method for modulating or treating at least one infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (A, B or C, or the like), septic arthritis, peritonitis, pneumonia, epiglottitis, e. coli 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium* intracellulare, *pneumocystis carinii* pneumonia, pelvic inflammatory disease, orchitis/epidydimitis, *legionella*, lyme disease, influenza a, epstein-barr virus, vital-associated hemaphagocytic syndrome, vital encephalitis/aseptic meningitis, and the like.

Any method of the present invention can comprise administering an effective amount of a composition or pharmaceutical composition comprising at least one anti-MCP-1 antibody to a cell, tissue, organ, animal or patient in need of such modulation, treatment or therapy. Such a method can optionally further at least one selected from at least one TNF antagonist (e.g., but not limited to a TNF antibody or fragment, a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anethetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod (dexamethasone), an anabolic steroid (testosterone), a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin (rituximab), an immunosuppressive (e.g., basiliximab, cyclosporine, daclizumab), a growth hormone, a hormone antagonist, a reproductive hormone antagonist (flutamide, nilutamide), a hormone release modulator (leuprolide, goserelin), a hormone replacement drug, an estrogen receptor modulator (tamoxifen), a retinoid (tretinoin), a topoisomerase inhibitor (etoposide, irinotecan), a cytoxin (doxorubicin), a mydriatic, a cycloplegic, an alkylating agent (carboplatin), a nitrogen mustard (melphalen, chlorabucil), a nitrosourea (carmustine, estramustine) an antimetabolite (methotrexate, cytarabine, fluorouracil), a mitotic inhibitor (vincristine, taxol), a radiopharmaceutical (Iodine 131-tositumomab), a radiosensitizer (misonidazole, tirapazamine) an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine (interferon alpha-2, IL2) or a cytokine antagonist (infliximab). Suitable dosages are well known in the art. See, e.g., Wells et al., eds., Pharmacotherapy Handbook, $2^{nd}$ Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Particular combinations for treatment of neoplastic diseases comprise co-administration or combination therapy by administering, before concurrently, and/or after, an antineplastic agent such as an alkylating agent, a nitrogen mustard, a nitrosurea, an antibiotic, an anti-metabolite, a hormonal agonist or antagonist, an immunomodulator, and the like. For use in metastatic melanoma and other neoplastic diseases, a preferred combination is to co-administer the antibody with dacarbazine, interferon alpha, interleukin-2, temozolomide, cisplatin, vinblastine, Imatinib Mesylate, carmustine, paclitaxel and the like. For metastatic melanoma, dacarbazine is preferred.

Therapeutic Treatments

Typically, treatment of pathologic conditions is effected by administering an effective amount or dosage of at least one anti-MCP-1 antibody composition that total, on average, a range from at least about 0.01 to 500 milligrams of at least one anti-MCP-1 antibody per kilogram of patient per dose, and preferably from at least about 0.1 to 100 milligrams antibody/kilogram of patient per single or multiple administration, depending upon the specific activity of contained in the composition. Alternatively, the effective serum concentration can comprise 0.1-5000 µg/ml serum concentration per single or multiple adminstration. Suitable dosages are known to medical practitioners and will, of course, depend upon the particular disease state, specific activity of the composition being administered, and the particular patient undergoing treatment. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 µg/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (compositions) suitable for internal administration generally contain from about 0.1 milligram to about 500 milligrams of active ingredient per unit or container. In these pharmaceutical compositions the active ingredient will ordinarily be present in an amount of about 0.5-99.999% by weight based on the total weight of the composition.

15. Diagnostic and Research Applications.

For diagnostic applications, the antibodies of the invention typically will be labeled with a detectable moiety. The detectable moiety can be any one which is capable of producing, either directly or indirectly, a detectable signal. For example, the detectable moiety may be a radioisotope, such as $^3H$, $^{14}C$, $^{32}P$, $^{36}S$, or $^{126}I$, a fluorescent or chemiluminescent compound, such as fluorescein isothiocyanate, rhodamine, or luciferin; radioactive isotopic labels, such as, e.g., $^{125}I$, $^{32}P$, $^{14}C$, technicium, or $^3H$, or an enzyme, such as alkaline phosphatase, beta-galactosidase or horseradish peroxidase.

Any method known in the art for separately conjugating the antibody to the detectable moiety may be employed, including those methods described by Hunter, et al., Nature 144:945 (1962); David, e at., Biochemistry 13:1014 (1974); Pain, et al., J. Immunol. Meth. 40:219 (1981); and Nygren, J. Histochem. and Cytochem. 30:407 (1982).

The antibodies of the present invention may be employed in any known assay method, such as competitive binding assays, direct and indirect sandwich assays, and immunoprecipitation assays. Zola, Monoclonal Antibodies: A Manual of Techniques, pp. 147-158 (CRC Press, Inc., 1987).

Competitive binding assays rely on the ability of a labeled standard (which may be alpha.v or an immunologically reactive portion thereof) to compete with the test sample analyte (alpha.v) for binding with a limited amount of antibody. The amount of MCP-1 in the test sample is inversely proportional to the amount of standard that becomes bound to the antibodies. To facilitate determining the amount of standard that becomes bound, the antibodies generally are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three part complex. David & Greene, U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case the detectable moiety is an enzyme.

The antibodies of the invention also are useful for in vivo imaging, wherein an antibody labeled with a detectable moiety such as a radio-opaque agent or radioisotope is administered to, a host, preferably into the bloodstream, and the presence and location of the labeled antibody in the host is assayed. This imaging technique is useful in the staging and treatment of neoplasms or bone disorders. The antibody may be labeled with any moiety that is detectable in a host, whether by nuclear magnetic resonance, radiology, or other detection means known in the art.

Having generally described the invention, the same will be more readily understood by reference to the following examples, which are provided by way of illustration and are not intended as limiting.

EXAMPLE 1

Generation of Murine Anti-Human MCP-1 Monoclonal Antibodies

In order to study the in vivo biology of anti-MCP-1 specific Mabs, a murine equivalent of an anti-human MCP-1 and rat equivalent of an anti-mouse JE (MCP-1 homolog) were prepared.

A C57BL/6 mouse was immunized with a DNA construct encoding human MCP-1 protein followed by injections with recombinant human MCP-1 (rHuMCP-1) protein. Splenocytes from the mouse demonstrating a specific IgG titer of 1:100,000 were fused with FO murine myeloma cells. Seven antibodies reactive to rHuMCP-1 were identified via EIA. The antibodies were further analyzed for the ability to inhibit MCP-1 induced chemotaxis of murine monocyte cells. Five Mabs appear to inhibit chemotaxis to a moderate degree, while the remaining two Mabs are non-inhibitors.

The varied characteristics of this panel of Mabs make some of them potential candidates to help define the benefits of MCP-1 blockade in models of MCP-1 dependent disease.

Human MCP-1 was cloned from human spleen by reverse transcription of polyA+ RNA (Clonetech) using AMV reverse transcriptase (Life Sciences) followed by amplification of the cDNA encoding MCP-1 via polymerase chain reaction using specific oligonucleotide primers. The primers corresponding to the 5' and 3' ends of MCP-1 cDNA contained Xba I and Bam HI restriction sites, respectively, to facilitate subcloning into the 072 intron A vector #1581. Individual colonies were isolated after transformation of *E. coli* DH10B, and several clones were subjected to DNA sequencing using an Applied Biosystems A310 automated DNA sequencer. One clone with the identical sequence to that found for human MCP-1 (NCBI NP_002973) was chosen for further use.

Purified plasmids were prepared at Puresyn, Inc. (Malvern, Pa.) and sent to Centocor. According to specification sheets provided by Puresyn Inc., the DNA homogeneity of the plasmids was 93% supercoiled based on scanning densitometry.

Immunization

A C57BL/6 mouse was treated with 1 mg rat anti-mouse IL-12 Mab (Mab C17.8, Centocor) and 5 mg pegylated recombinant mouse IL-4 (L-4 from R&D Systems, pegylated in-house) by intraperitoneal (IP) injection on day 0. The mouse was immunized on days 1 and 14 with 10 mg of human MCP-1 DNA construct diluted in PBS and given intradermally (ID) in the ear. On days 28 and 114, the mouse was boosted with 15 mg recombinant human MCP-1 protein (RDI) diluted in PBS and given subcutaneously (SQ).

The mouse was bled at various time-points throughout the immunization schedule. Blood collections were performed by retro-orbital puncture and serum was collected for titer determination by solid phase EIA.

Three days prior to fusion, the mouse was given a final IV booster injection of 10 mg rHuMCP-1 diluted in 100 mL PBS. The mouse was euthanized by $CO_2$ asphyxiation, and the spleen aseptically removed and immersed in 10 mL cold PBS/PSA (PBS containing PSA which is 100 U/ml penicillin, 100 mg/ml streptomycin, and 0.25 mg/ml amphotericin B). The splenocytes were harvested by sterilely perfusioning of the spleen with cold perfusion medium (DMEM, 20% FBS, 1 mM sodium pyruvate, 4 mM L-glutamine, 1% MEM nonessential amino acids, and 1% Origen (IGEN)). The cells were enumerated on a Coulter counter, washed once, and resuspended in 10 mL perfusion medium.

Cell Fusion

One fusion was performed with splenocytes from a mouse immunized with a DNA construct encoding human MCP-1 followed by boosts with recombinant human MCP-1 protein. The mouse demonstrated a specific IgG titer to human MCP-1 of 1:1,000,000 at the time of fusion.

A non-secreting Balb/c mouse myeloma fusion partner FO was purchased from ATCC (#CRL-1646). Prior to fusion, the myeloma cells were thawed and maintained at log phase in the media described above. On fusion day, the cells were washed in PBS, counted, and viability determined (>95%) via trypan blue dye exclusion.

Fusion was carried out at a 1:1 ratio of FO murine myeloma cells to viable spleen cells. Spleen and myeloma cells were mixed together and pelleted. The pellet was resuspended with 5 mL of 50% (w/v) PEG/PBS solution (using PEG molecular weight 3000) at 370 C. Cell fusion was allowed to occur for 2 minutes at 370 C. The fusion was stopped by slowly adding 25 mL DMEM (no additives) at 37° C. Fused cells were centrifuged for 5 minutes at 1000 rpm, drawn up into 25 mL pipet, and expelled into a 225 cm2 flask (Costar, 431082) containing 240 mL of Fusion Medium (DMEM, 20% FBS, 1 mM sodium pyruvate, 4 mM L-glutamine, 1% MEM nonessential amino acids, 1% Origen, 25 mg/ml gentamicin, 100 mM hypoxanthine, 0.4 mM aminopterin, and 16 mM thymidine). The cells were allowed to sit for 4 hours at 37° C, an additional 360 mL of 37° C Fusion Medium was added to the flask, and the flask was swirled to resuspend the cells. The cells were then seeded at 200 mL/well in thirty 96-well flat bottom tissue culture plates (Costar, 3595). The fusion plates were placed in a humidified 37° C incubator at 5% $CO_2$ for 7-10 days. The media was changed by taking off 100 mL medium adding 100 mL HT medium after 7 days.

Detection of Murine Anti-Human MCP-1 IgG Antibodies in Mouse Sera

ELISA was used to quantify murine anti-human MCP-1 antibodies in the sera of MCP-1 immunized mice. Briefly, wells (Nunc-immunoPlate, 446612) were coated with 100 uL of rHuMCP-1 (RDI, RDI-304) at 10 mg/mL in PBS, pH 7.4 and incubated overnight at 4° C. The plates were washed three times in 0.15M saline with 0.02% v/v Tween 20, and then blocked with 200 mL/well I-Block (0.2%) (Tropix, A1300)+0.05% Tween-20 (0.05%) diluted in 1×PBS for 2 hours at room temperature. Serial dilutions of sera (diluted in I-Block) were incubated on the plates for 2 hours in a volume of 100 mL/well. Subsequently, the plates were washed as before and bound antibodies detected with 100 mL/well of the rabbit-anti-mouse-HRP labeled IgM or IgG secondary reagents (Zymed, 61-6820 & 61-6020) diluted 1:4000 in I-Block and incubated at room temperature for 1-2 hours. The plates were then washed and the substrate developed for approximately 20 minutes with 100 mL/well TMB-S (RDI-TMB-S-1L). The reaction was stopped with the addition of 25 mL/well of $H_2SO_4$. The absorbance was measured at dual wavelengths of 450 and 550 by an automated plate Thermomax spectrophotometer (Molecular Devices).

Detection of Murine IgG Anti-Human MCP-1 Antibodies in Hybridoma Supernatant

Hybridomas were evaluated by EIA for their ability to secrete anti-HuMCP-1 antibodies. Briefly, plates were coated with rHuMCP-1 at 1 mg/mL in PBS overnight at 4° C, washed and blocked with 200 uL/well of 1% bovine serum albumin (BSA) in PBS for 1 hour at 37° C. The plates were used immediately or stored at −20° C. Undiluted hybridoma supernatants were incubated on plates for 30 minutes at RT. All fusion plates were tested. The plates were washed and then probed with 50 mL/well HRP-labeled goat anti-mouse IgG Fc specific antibody (Sigma) diluted 1:20,000 in 1% BSA-PBS for 30 minutes at 37° C. The plates were washed again and incubated with 100 mL/well of citrate-phosphate substrate solution (0.1M citric acid, 0.2M sodium phosphate, 0.01% $H_2O_2$, 1 mg/mL OPD (Sigma) was added for approximately 15 minutes at RT. The reaction was stopped by the addition of 25 mL/well, 4N $H_2SO_4$. The absorbance was measured at 490 nm by an automated plate spectrophotometer. Cells in positive wells were transferred to 24-well plates to increase cell numbers and later subcloned by limiting dilution.

Isotyping

Isotype determination of the antibodies was accomplished by use of the Mouse Monoclonal Antibody Isotyping Kit-IsoStrip, Dipstick Format (Roche cat#1 493 027). Briefly, culture supernatant was diluted 1:10 in PBS and added to the development tube. The dipstick was added to the development tube and incubated at RT for approximately 10 minutes. Isotype were determined by visual assessment following incubation.

Neutralization Capability of Murine Anti-Human MCP-1 Antibodies: MCP-1 Induced Chemotaxis Generally, a number of small molecules, chemokines, and cytokines, and growth factors, are known to stimulate movement (chemotaxis) of certain cell types allowing them to become flexible enough to pass through small pores. This property forms the basis of a standard in vitro assay. The attractant (MCP-1) is placed in the bottom well of a disposable 8 um Neuroprobe chemotaxis chamber (~315 ul). The filter is overlaid with a known number of cells. After applying stimulus, the number of cells appearing on the opposite surface of the filter are quantitated.

THP-1 murine monocyte cells that are known to migrate in response to MCP-1 were cultured in Vitacell (30-2001, ATCC)RPMI+10% FBS at a density of $4-8×10^5$/ml. The cells were harvested and resuspended in 10 mL of culture media containing 25 mL of a 1 mg/mL solution of calcein-am (C-3099, Molecular Probes) for 1 hour at 37° C. Recombinant human MCP-1 (R&D Systems, catalog 279-MC) at 100 ng/mL +/− serial dilutions of antibody were loaded into the bottom wells of a Neuroprobe disposable chemotaxis plate (116-8, Neuroprobe). Antibodies included purified candidates or a commercial Mab (R&D Systems, catalog MAB279) that was used as a positive control. An 8 micron polycarbonate filter was applied to the plate and $1×10^6$ calcein loaded THP-1 cells were added on each surface well in a volume of 50 mL. Cells were allowed to migrate for 1 hour at 37° C., 5% $CO_2$. Cells were rinsed off the top of the filter with water and the whole plate analyzed using the SPECTRAFluor Plus with the excitation filter set to 485 nm and the emission filter set to 535 nm.

For murine MCP-1 chemotaxis assay, THP-1 murine monocyte cells that are known to migrate in response to MCP-1 were cultured in Vitacell (30-2001, ATCC)RPMI+10% FBS at a density of $4-8×10^5$/ml. The cells were harvested and resuspended in 10 ml of culture media containing 25 ml of a 1 mg/ml solution of calcein-am (C-3099, Molecular Probes) for 1 hour at 37° C. Murine MCP-1 (R&D Systems, catalog 479-JE) at a concentration of 10 ng/ml +/− serial dilutions of antibody were loaded into the bottom wells of a Neuroprobe disposable chemotaxis plate (116-8, Neuroprobe). Antibodies included purified Mabs or a commercial polyclonal anti-murine MCP-1 (R&D Systems, catalog AF-479-NA) as a positive control. An 8 micron polycarbonate filter was applied to the plate and $1×10^6$ calcein loaded THP-1 cells were added on each surface well in a volume of 50 ml. Cells were allowed to migrate for 1 hour at 37° C., 5% CO2. Cells were rinsed off the top of the filter with water and the whole plate analyzed using the SPECTRAFluor Plus with the excitation filter set to 485 nm and the emission filter set to 535 nm.

Results

A total of 7 antibodies specific for human MCP-1 were identified via EIA (ELISA) from the fusion designated MHMCP1. All seven Mabs were of the IgG1 kappa isotype. The murine anti-human MCP-1 Mabs were analyzed for their ability to inhibit the chemotactic effect of MCP-1 on THP-1 murine monocyte cells. Five Mabs demonstrated moderate to complete inhibition of MCP-1 induced chemotaxis as compared with a commercial positive control antibody (R&D Systems). The remaining two Mabs did not inhibit chemotaxis.

All hybrids and Mabs were assigned C code and CNTO numbers respectively and the cell lines were banked. Table 1 summarizes the fusion results.

TABLE 1

| C Code | CNTO# | Isotype | Conc. Dependent Inhibition in the Chemotaxis assay |
|---|---|---|---|
| C775 | 4874 | IgG1κ | Y |
| C753 | 843 | IgG1κ | Y |
| C752 | 619 | IgG1κ | Y |
| C730 | 1110 | IgG1κ | N |
| C729 | 2723 | IgG1κ | N |
| C728 | 7221 | IgG1κ | Y |
| C727 | 1316 | IgG1κ | Y |

EXAMPLE 2

Radioligand Binding Assay for Screening Anti-MCP-1 Antibodies

A radionuclide-labeled ligand binding assay, which measures the resulting CPM of 125I labeled MCP-1 binding to its receptor CCR2 on the monocytic cell line THP-1 was developed. Furthermore this assay can be used to identify MCP-1 neutralizing Mabs.

MCP-1 is known to bind and signal through the chemokine receptor, CCR2. CCR2 is a seven trans-membrane-spanning G-protein-coupled receptor expressed on many cells including monocytes, T-cells, B-cells, and basophils. Two MCP-1 specific receptors, CCR2A and CCR2B, have been cloned which signal in response to nanomolar (nM) concentrations of MCP-1

The human monocytic cell line, THP-1, expresses CCR2 at an appreciable density, as demonstrated by flowcytometry. We believe that THP-1 cells express the CCR2B receptor. THP-1 cells were used in an assay for selecting neutralizing anti-MCP-1 Mabs by measuring the binding capacity of $^{125}$I MCP-1 to its receptor CCR2 on THP-1 cells and the ability of anti-MCP-1 Mabs to block this binding.

Materials and Methods

THP-1 cells (TIB-202, ATCC, Manassas, Va.) are a human leukemic cell line cultured from the blood of a patient with acute monocytic leukemia. THP-1 cells were maintained in culture at 37° C. and 5% $CO_2$. The cells were cultured in RPMI 1640 medium with 2 mM L-glutamine adjusted to contain final concentrations of 1.5 g/L sodium bicarbonate, 4.5 g/L glucose, 10 mM HEPES and 1.0 mM sodium pyruvate, 90%; 10% fetal bovine serum. (Vitacell RPMI 20-2001, ATCC, Manassas, Va.). The cells were maintained at a density of $4-8 \times 10^5$ cells/ml and did not exceed $1 \times 10^6$ cells/ml. Cell culture media was renewed every 2-3 days and the doubling time was approximately 26-30 hours.

Assay buffer was prepared by adding 10 ml of 10% bovine serum albumin (BSA) (A1595, Sigma, St. Louis, Mo.) to 1 liter RPMI Medium 1640 with Glutamax and 25 mM HEPES (72400-047, Invitrogen Corp., Grand Island, N.Y.) resulting in RPMI with 0.1% BSA. Wash Buffer was prepared by adding 24 g NaCl to 1 liter of Assay Buffer.

$^{125}$I MCP-1 (NEX332, Perkin Elmer Life Sciences, Inc., Boston, Mass.): 125I MCP-1 was diluted in assay buffer and used at a final concentration of 1 ng/ml in assays to assess Mab neutralization. Dilutions of cold MCP-1 (MCP-1 279-MC, R&D Systems, Minneapolis, Minn.): were made in assay buffer and used at a final concentration of 10 mg/ml to assess non-specific binding of 125I MCP-1. Serial dilutions of the commercial Mab (Anti-MCP-1 MAB279, R&D Systems, Minneapolis, Minn.) were made in working buffer at varying concentrations. Serial dilutions of all test Mabs were made in assay buffer at varying concentrations.

Binding Assay Protocol

The binding assay was performed in a 96-well format, using Millipore filter plates (MABVN1250, Milllipore, Bedford, Mass.). For the assay, THP-1 cells in assay buffer were plated (50 ml/well) at a density of $2 \times 10^7$ cells/ml ($1 \times 10^6$ cells/well).

The following procedure was used:

Negative controls (no inhibition) or total binding was measured in 50 ul of assay buffer with no other additions. Nonspecific binding (background) was measured by adding 50 ul of MCP-1 at a final concentration of 10 mg/ml. Test wells received 50 ul of serial dilutions of mAb. Lastly, 50 ul of 125I MCP-1 at a final concentration of 1 ng/ml was added to all wells resulting in a total assay volume of 150 ml.

Cells were incubated for 1 hour at room temperature (RT). The plate was then placed on a vacuum manifold (MAVM0960R, Milllipore, Bedford, Mass.) and washed 3 times with 150 ul of wash buffer. The plate gasket was removed and the filters allowed to air dry. Filters were then punched out using disposable punch tips (MADP19650, Millipore, Bedford, Mass.) and the Multiscreen multiple punch (MAMP09608, Millipore, Bedford, Mass.) into 4 ml vials. The filters were then counted using the Wallac Wizard 1470 Automatic Gamma Counter (1470-010, Perkin Elmer Life Sciences Inc., Boston, Mass.)

Data analysis. Counts per minute (CPM) values in total binding wells were considered to be 100% binding. CPM values in non-specific binding wells were considered background or 0% binding. Percent inhibition of the total binding by the varying doses of each mAb were calculated. The percent inhibition values were then imported into the Graphpad Prism program and plotted using a sigmoid dose-response curve with a variable slope and constants of bottom=0 and top=100. The resulting IC50 value, which is the concentration at which the observed binding is 50% of total binding, was recorded.

Initially, experiments were performed to establish the optimal conditions for the binding assay. Firstly, the optimal cell density was established by comparing the ratio of total:nonspecific binding of three cell densities, $5 \times 10^5$, $7.5 \times 10^5$, and $1 \times 10^6$ cells/well and using $^{125}$I MCP-1 at 0.1, 1, or 10 ng/ml with excess cold MCP-1 at 10 mg/ml. From this experiment, a cell density of $1 \times 10^6$ was identified as the concentration that gave the highest percentage of specific binding with the lowest amount of $^{125}$I MCP-1 tested in this assay. This optimal cell concentration was used for all subsequent studies.

MCP-1 Kd Determination. In order to identify the optimal concentration for antibody neutralization testing, we established the dissociation constant (Kd) of $^{125}$I MCP-1 in the binding assay on THP-1 cells at a density of $1 \times 10^6$ cells/well. Increasing amounts of $^{125}$I MCP-1 were incubated with or without an excess (10 mg/ml) of unlabelled MCP-1 together with THP-1 cells. The specific bound $^{125}$I MCP-1 was calculated and plotted against the total concentration of $^{125}$I MCP-1. A Kd of 8.964 ng/ml (60 pM based on 150 kDa Mol wt) was calculated using a one-site binding hyperbola curve fit (FIG. 1). In order to test the neutralization capacities of the antibodies in this assay at a concentration below the Kd of MCP-1 and based on the results of the cell number optimization study, a concentration of 1 ng/ml $^{125}$I MCP-1 was established as optimal.

Neutralization of $^{125}$I MCP-1 Binding by Anti-MCP-1 Mabs.

To test the efficacy of anti-MCP-1 mabs, a concentration of 1 ng/ml $^{125}$I MCP-1 was used. Cells were incubated with 1 ng/ml $^{125}$I MCP-1 with or without serial dilutions of either the commercial Mab (positive control) or 6 different Mabs generated in Example 2. There is a dose-dependent inhibition of $^{125}$I MCP-1 binding to the CCR2 receptor with the commercial Mab. A dose-dependent inhibition was also observed with five of the six Centocor-generated Mabs allowing the calculation of an IC50 concentration: C727, C728, C752, C753 and, C775. However, C730 was not effective at neutralizing this binding, demonstrating that the assay is able to distinguish between antibody efficacies. IC50 values were generated from these data and are shown in Table 2. These data demonstrate that this is a robust assay, which allows us to distinguish between the activities of different Mabs.

TABLE 2

| Mab | C Code | $IC_{50}$ (ug/ml) | $IC_{50}$ (nM) |
| --- | --- | --- | --- |
| CNTO1316 | C727 | 7.4 | 49 |
| CNTO7221 | C728 | 3.5 | 14 |
| CNTO619 | C752 | 6.45 | 43 |
| CNTO843 | C753 | 18.35 | 122 |
| CNTO4874 | C775 | 7.1 | 47 |
| CNTO1110 | C730 | >200 | >1333 |
| Commercial Mab | | 48.97 | 326 |

EXAMPLE 3

Calcium Mobilization Assay for Selecting Anti-MCP-1 Antibodies

A calcium mobilization assay, which measures the intracellular mobilization of calcium as a result of MCP-1 binding to its receptor CCR2 on the monocytic cell line THP-1 is described. The method described uses time-resolved fluorescence changes using the FLEXstation™ (Molecular Devices, Sunnyvale, Calif.), which features an integrated fluid transfer capability from a source plate or a reservoir to an assay plate with concurrent kinetic fluorometric analysis of reactions. The instrument is controlled by an external personal computer running the SOFTmax PRO software, which provides integrated instrument control, data display, and statistical data analysis. Furthermore this assay can be used to identify MCP-1 neutralizing Mabs.

Materials and Methods

THP-1 cells were acquired and maintained as described in Example 3. THP-1 cells were assessed for CCR2 receptor expression in the following way: $2 \times 10^6$ cells/ml in PBS+ 0.5% BSA were blocked with Human Purified IgG 4 mg/ml 2 mg per reaction by incubating the IgG with cells for 15 minutes at RT. Then either anti-CCR2 conjugated to PE (R&D Systems, #FAB151P) or the isotype control (R&D Systems, #IC004P) was incubated with the cells on ice for 35 min. in the dark. 4 ml of PBS was then added to each reaction and the tubes were centrifuged for 7 min at 900 rpm. The sups were decanted and the cells were resuspended in 400 ml of PBS and kept on ice until the FACS analysis was performed.

Ca2+ Assay Reagents

FLEXSTATION™ Ca2+ Plus Assay Kit (#R8051, Molecular Devices, Sunnyvale, Calif.) is a fluorescence based assay kit for detecting changes in intracellular calcium specifically designed for use with chemokine and other small peptide receptors and works with both adherent and non-adherent cell types. The kit contains a) 10× Reagent Buffer Component B—10× Hanks Buffered Salt Solution with 200 mM HEPES pH6.0; stored at 4° C. b) FLEXstation Calcium Assay Reagent (Component A) a proprietary reagent; stored at −20° C.

Additional reagents include: probenecid, inhibitor of anion-exchange channel (P8761, Sigma, St. Louis, Mo.). Probenecid was prepared fresh on the day of the assay in the following way: 710 mg Probenecid was dissolved in 5 ml 1N NaOH followed by the addition of 5 ml of 1× Reagent Buffer. Working Buffer was prepared by adding 1 ml of Probenecid to 99 ml of 1× Reagent Buffer (1:100 dilution). This working buffer was used for all ligand dilutions and to make the loading buffer. Loading Buffer was prepared in the following manner: one vial of FLEXstation Ca2+ Plus Assay Reagent (Component A) was removed from the −20° C. freezer and allowed to equilibrate to RT. Loading buffer was prepared by adding 10 ml of working buffer containing probenecid to the vial and vortexed. Poly-D-lysine was used for plate coating to improve cell adherence (P7405, Sigma, St Louis, Mo.) and was prepared in the following manner: 5 mg of Poly-D-Lysine was dissolved in 25 ml dH2O by vortexing. The calcium ionophore, ionomycin, was used as a positive control for cell labeling. Ionomycin was stored at 4° C. at a concentration of 5 mg/ml in DMSO. 825 ml of Working Buffer was added to 25 ml of the ionomycin resulting in a 150 mg/ml solution.

Antibody reagents were: the positive control antibody was anti-MCP-1 (MAB279, R&D Systems, Minneapolis, Minn.) diluted serially in working buffer; test anti-human MCP-1 Mabs (Example 2) diluted serially in working buffer; and Control antibody was a mouse IgG1 Isotype Control (Southern Biotech, 0102-14). Antibodies were tested in the presence of 300 ng/ml MCP-1.

Ca2+ Assay Protocol

The Ca2+ mobilization assay was performed in a 96-well format, using black-sided, clear-bottom plates (29433-152, VWR, West Chester, Pa.). The plates were prepared by adding Poly-D-Lysine (50 ml/well) and incubated at RT for 1 hour. Plates were inverted and washed with 150 ml dH2O. The plates were dried at RT for 4 hours and stored at 4° C. until use for a maximum of 3 months.

For the assay, cells (in cell culture media) were plated (100 ml/well) in the Poly-D Lysine-coated plates a density of $1-2 \times 10^6$ cells/ml. The cells were then loaded with fluorophore by the addition of 100 ml/well of loading buffer, resulting in a total volume of 200 ml in each well. Cells were incubated for 1 hour at 37° C. and 5% CO 2.

During the incubation of the loading buffer with the cells, a second 96-well addition plate was prepared. This plate contained either varying concentrations of MCP-1 or, when Mabs were assayed, MCP-1 at 300 ng/ml and varying concentrations of Mab. Ionomycin was added to additional wells (7.5 mg/well) as a positive control.

Following incubation of the cells, a cell monolayer was achieved by centrifugation (1200 rpm, 4 minutes, no break). After spinning, the plate was placed back in the incubator for 5 minutes after which the cell plate and the addition plate were loaded into the FLEXstation for measurement of Ca2+ mobilization.

FLEXstation Setup

THP-1 cells have been shown to express CCR2 in the literature (Wang, G. et al. 2001 Biochem J 357: 233-40)). This observation was confirmed as THP-1 cells incubated with anti-CCR2 antibody labeled with PE (phycoerythrin; solid line) were approxiamately 10-fold brighter than those incubated with isotype control antibody by FACS analysis. Next, conditions for optimization of the Ca2+ mobilizatiron were established. The parameters include: cell density at plating ($2\times10^5$), concentration of MCP-1 used for stimulation (response curve was maximal and flattened at 1 ug/ml and above, therefore 300 ng/ml were used and give reproducible results), speed of additon of the ligand based on instrument settings, and peak fluorescence based on the time course of the Ca2+ flux. The optimized experimental setup parameters were as follows:

Wavelength Parameters ($Ca^{2+}$ Plus Assay Kit Recommendations):

| Parameters | Setting |
| --- | --- |
| Excitation Wavelength (nm) | 485 |
| Emission Wavelength (nm) | 525 |
| Emission cut-off (nm) | 515 |

The temperature is 37° C. (set on the FLEXstation control panel, must be set 10 minutes before assay is run to let machine equilibrate). The Sensitivity Parameters are Sensitivity=Normal–5 and PMT Sensitivity is HIGH.

Timing Parameters

| Parameters | Setting |
| --- | --- |
| Run Time (sec) | 100 |
| Interval (sec) | 1.5 |
| Number of Reads | 67 |
| Minimum Interval | 1.44 |
| Minimum Run Time (sec) | 42 |

Ligand Addition Parameters

| Parameters | Setting |
| --- | --- |
| Number of Additions | 1 |
| Initial Volume (uL) | 200 |
| Pipette Height (uL) | 210 |
| Transfer Volume (uL) | 50 |
| Concentration of Ligand (fold) | 5X |
| Concentration of Mab and Ligand when added together | 10X of each |
| Addition Speed (Rate) | 1 |
| Addition Time point (sec) | 18 |

Running the FLEXstation Ca2+ Assay

The assay plate was transferred directly to the FLEXstation assay plate carriage, which had been pre-warmed to 37° C., and the assay was run using the parameters described above. For stimulation of Ca2+ mobilization, MCP-1 (dose range; duplicate or triplicate wells per concentration) was added in the absence or presence of Mab. Ionomycin was included on each plate as a positive control for the detection system. MCP-1 at 300 ng/ml was run in each column as a positive control where Mab neutralization potential was assayed.

The data are expressed as the peak of the Ca2+ flux. This is the difference between the maximum (Max) RFU obtained and the mean of the RFU values taken at the first three time points. The peak RFU values were imported into the Microsoft Excel program. Percent inhibition of the Ca2+ response by the varying concentrations of each Mab were calculated. The percent inhibition values were then imported into the Graphpad Prism program and plotted using a sigmoid dose-response curve with a variable slope and constants of bottom=0 and top=100. The resulting IC50 values were recorded.

Results

Figure 2A:
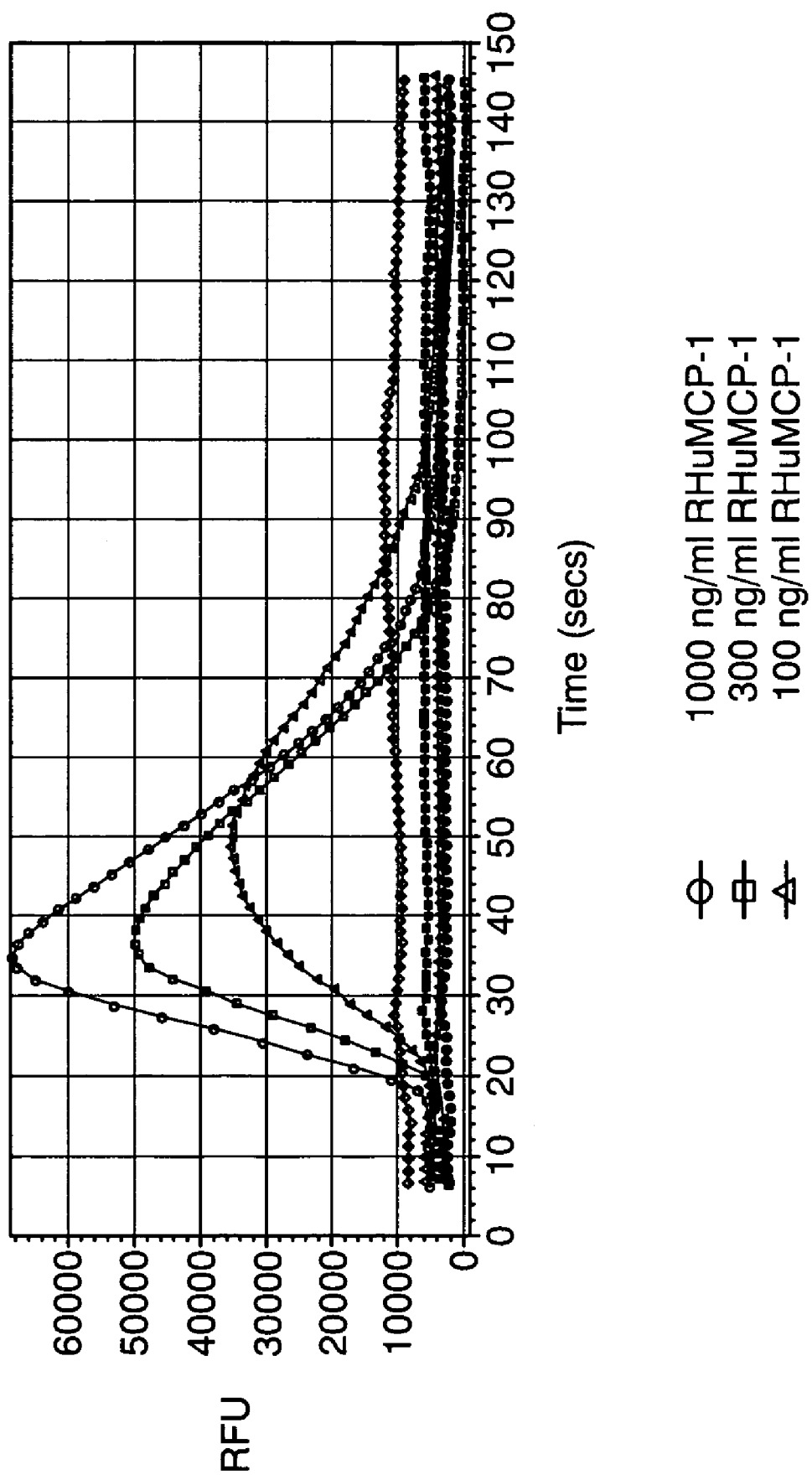
FIG. 2 shows a) plots of the relative fluorescence emitted by cells stimulated with MCP-1 over time and b) shows curves fit to fluorescence data from cells stimulated by MCP-1 in the presence of various anti-MCP-1 antibodies.
Figure 2B:
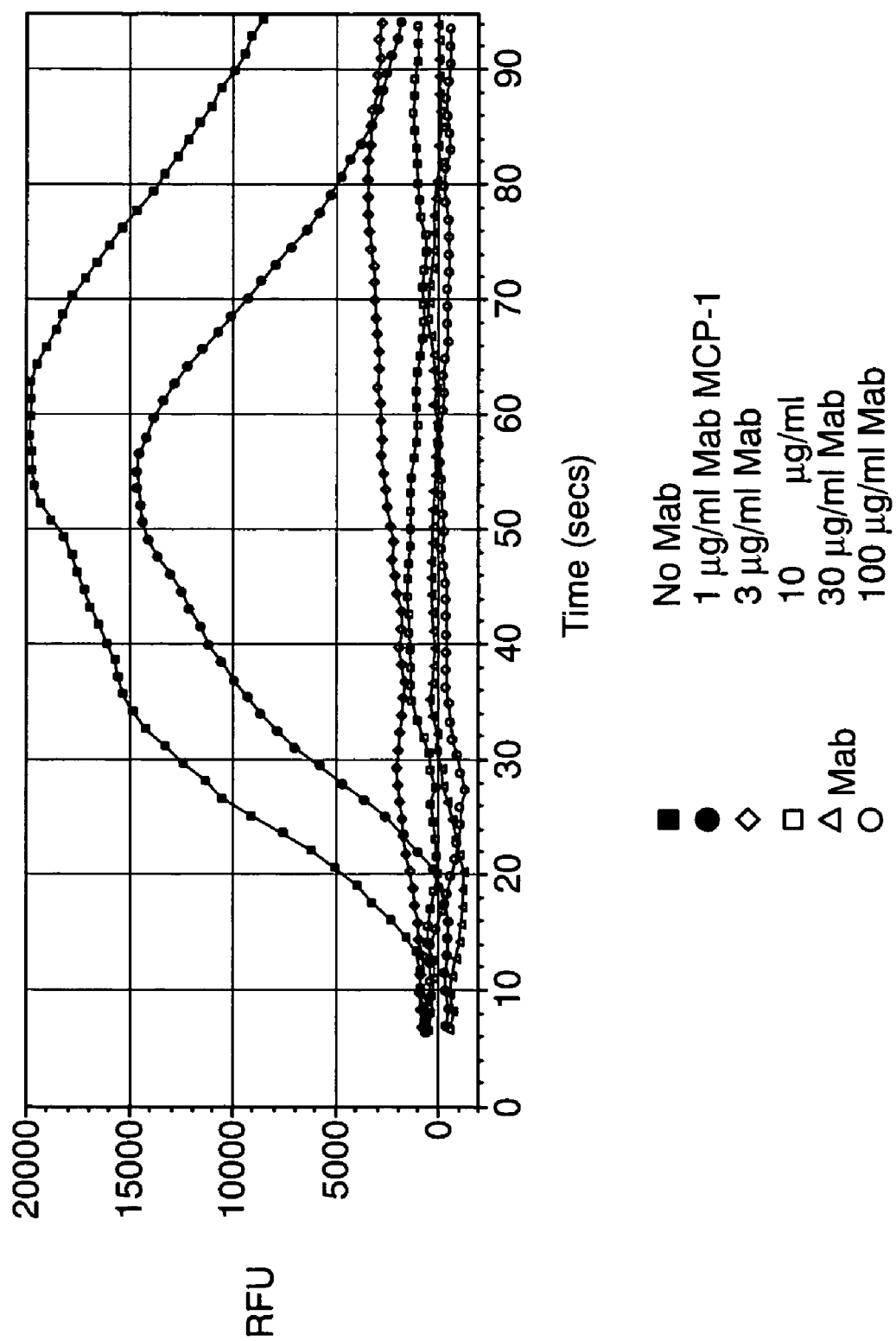

MCP-1, 300 ng/ml, was pre-incubated in a 96 well plate with serial dilutions of the commercial Mab (positive control) or 5 different test Mabs generated at Centocor. Mabs (0-100 mg/ml in ½ log dilutions). MCP-1 and Mab were added at time=18 seconds to the cells. The data are represented as either real-time RFU values at each time point which were measured every 1.5 seconds in a single experiment (FIG. 2a) or, as percent inhibition of the peak RFU value from one experiment. Concentration-dependent inhibition was similarly observed with four of the five Centocor-generated Mabs (FIG. 2b); CNTO1316, CNT07221, CNTO619 and, CNT04874. However, CNTO2723 was not effective at neutralizing Ca2+-mobilization in response to MCP-1. The mouse isotype control IgG1 had no effect on the Ca2+ response (data not shown). IC50 values were generated from these data and are shown in Table 3 (molarity is based on an average weight of 150 kDa for each Mab). These data demonstrate that the assay is robust enough to allow the antibodies to be distinguished on the basis of this activity.

TABLE 3

| Mab | C-Code | $IC_{50}$ (µg/ml) | $IC_{50}$ (nM) |
| --- | --- | --- | --- |
| CNTO1316 | C727 | 13.58 | 91 |
| CNTO7221 | C728 | 5.07 | 38 |
| CNTO2723 | C729 | >100 | >667 |
| CNTO619 | C752 | 2.26 | 15 |
| CNTO4874 | C775 | 8.01 | 53 |
| Commercial Mab | NA | 2.37 | 16 |

EXAMPLE 4

Demonstration of Specific Binding for Human MCP-1

Anti-MCP-1 monoclonal antibodies were captured onto a BIAcore CM5 sensor surface (Biacore International, Piscataway, N.J.). A solution containing a mixture of rabbit anti-human Fc specific polyclonal antibodies and rabbit anti-mouse Fc specific polyclonal antibodies was first immobilized onto the sensor surface. After the restabilization of the new baseline, the anti-MCP-1 mAb is passed over the surface.

Human MCP-1 purchased from R&D Systems (www.rnd-systems.com) was reconstituted as proscribed by the vendor. Samples of varying concentrations were prepared using this stock solution. They were then passed over the surface of captured anti-MCP-1 mAb using KINJECT command at a flow rate of 30 uL. Measurements are typically performed at 25° C. Sensor data was analyzed using the BLAevaluation software provided with the instrument.

Characterization of mAb Specificity

Analysis is performed as described above, with the exception only a single concentration is used, typically, a high ligand concentration (100 nM). Chemokines selected for mAb specificity were human forms of MCP-1, MCP-2, Eotaxin-1, Eotaxin-2 (CCL24, MPIF-2, NP_002982) and Eotaxin-3 (CCL26, GenBank Q9Y258). All chemokines were purchased from R&D Systems. Dextran-sulfate (1%) was added to the sample buffer in the final round of assays to reduce non-specific binding, particularly to eotaxin-3.

The BIAcore instrument can also be used to demonstrate complementation groups or epitope map the binding of various antibodies to there target. The assay determines if MCP-1 bound to one mAb is capable of binding with another mAb. The assay is performed by capturing the first mAb onto a surface of immobilized rabbit antimouse Fc specific polyclonal antibody. The surface is then treated with mouse IgG to mask any remaining anti-mouse Fc binding sites on the surface. MCP-1 is then passed over the surface, binding to the first mAb. Immediately, after the injection of the MCP-1, the second mAb is passed over the surface. The amount of second mAb bound to the MCP-1 is then recorded. The assay is then repeated, reversing the order of the mAbs.

The data for binding of C775 to each of the ligand described was processed to give a binding constant, where measurable. There was no measurable binding of C775 to any of the other MCP-1 homologs or eotaxin homologs. The calculated binding constant of C775 to MCP-1 by this method was 1.0 nM and for eotaxin >5 uM, respectively, for a ligand concentration 100 nM. Therefore, the binding specificity of C775 for MCP-1 as compared to eotaxin is >5000 fold. Eotaxin-1 and MCP-1 have the highest sequence identity of any of these pairs of polypeptides, therefore, it was concluded that the specificity of C775 for MCP-1 as compared to all tested homologs was >5000-fold.

EXAMPLE 5

Preparation of Rat Anti-Mouse JE (Murine MCP-1 Homolog)

Evaluation of the effectiveness and utility of anti-human MCP-1 antibody therapy necessitates the use of animal models. Consequently, Sprague Dawley rats were immunized the murine the MCP-1 homolog, JE, to generate antibodies that can serve as potential surrogates in mouse model systems. In human xenografts models, the antibodies could serve to distinguish between graft effects and host effects of the protein under study.

Materials and Methods

Twenty-week old Sprague Dawley rats housed and cared for at Covance Research Products Inc (Denver, Pa.) were immunized subcutaneously with rMuMCP-1 (R&D Cat# 479-JE/CFz). Each rat was injected with a 0.5 mL combination of rMuMCP-1, Benadryl (Sigma), and Freund's Adjuvant (Sigma) divided between 2 injection sites given intradermally (ID) and intraperitoneally (IP). The prescribed immunization protocol was for each rat to receive a total of 9 injections over a 9-month timeframe. The first and second injections consisted of 50 mg rMuMCP-1 in 250 mL PBS+ 36 mL Benadryl emulsified with an equal volume of Complete Freund's adjuvant. For the rest of the injections, each rat received 50 mg rMuMCP-1+ Benadryl as before with the exception of Incomplete Freund's Adjuvant.

The rats were bled at various time-points throughout the immunization schedule. Blood collections were performed by retro-orbital puncture and serum was collected, frozen, an shipped on dry ice to Centocor for titer determination by solid phase EIA. Five days following the 9th injection, two rats were shipped to Centocor. The rats were given a final IV booster injection of 10 mg rMuMCP-1 diluted in 120 mL PBS two days after arrival at Centocor.

Two fusions were performed with rat splenocytes from animals immunized with murine MCP-1. Each rat demonstrated specific IgG titers to murine MCP-1 of >1:10,000 at the time of fusion. Three days later the rats were euthanized by $CO_2$ asphyxiation, and the spleens aseptically removed and immersed in 10 mL cold PBS/PSA (PBS containing PSA which is 100 U/ml penicillin, 100 mg/ml streptomycin, and 0.25 mg/ml amphotericin B). The splenocytes were harvested by sterilely perfusing the spleen with cold perfusion medium (DMEM, 20% FBS, 1 mM sodium pyruvate, 4 mM L-glutamine, 1% MEM nonessential amino acids, and 1% Origen (IGEN)). The cells were enumerated on a Coulter counter, washed once, and resuspended in 10 mL perfusion medium.

Mouse Myeloma Cell Lines

The non-secreting mouse myeloma fusion partner, P3×63 Ag 8.653 (653) was used. The cell line was expanded in RPMI 1640 medium (JRH Biosciences) supplemented with 10% (v/v) FBS (Cell Culture Labs), 1 mM sodium pyruvate, 0.1 mM NEAA, 2 mM L-glutamine (all from JRH Biosciences) and cryopreserved in 95% FBS and 5% DMSO (Sigma), then stored in a vapor phase liquid nitrogen freezer in CBS. The cell bank was sterile (Quality Control Centocor, Malvern) and free of mycoplasma (Bionique Laboratories).

A cell bank of the non-secreting Balb/c mouse myeloma fusion partner FO was purchased from ATCC (# CRL-1646). One frozen vial of FO cells was received at Centocor Malvern Cell Biology Services (CBS) group, thawed and resuspended in aMEM (modified) medium (JRH Biosciences) supplemented with 10% (v/v) FBS (Cell Culture Labs), 1 mM sodium pyruvate, 0.1 mM NEAA, 2 mM L-glutamine (all from JRH Biosciences). The cells were expanded, cryopreserved in 95% FBS and 5% DMSO (Sigma) and stored in a vapor phase liquid nitrogen freezer in CBS. The cell bank was sterile (Quality Control Centocor, Malvern) and free of mycoplasma (Bionique Laboratories) (3).

Prior to fusion, myeloma cells were thawed and maintained at log phase in the media described above. On fusion day, the cells were washed in PBS, counted, and viability determined (>95%) via trypan blue dye exclusion.

Cell Fusion

Fusion was carried out at a 1:1 ratio of FO or 653 murine myeloma cells to viable spleen cells (Rat#C73 with FO, Rat#C74 with 653). Spleen and myeloma cells were mixed together and pelleted. The pellet was resuspended with 5 mL of 50% (w/v) PEG/PBS solution (using PEG molecular weight 1450 for rat #C74 fusion and PEG molecular weight 3000 for rat #C73) at 370 C. Cell fusion was allowed to occur for 2 minutes at 370 C. The fusion was stopped by slowly adding 25 mL DMEM (no additives) at 370 C. Fused cells were centrifuged for 5 minutes at 1000 rpm, drawn up into 25 mL pipette, and expelled into a 225 $cm^2$ flask (Costar, 431082) containing 240 mL of Fusion Medium (DMEM, 20% FBS, 1 mM sodium pyruvate, 4 mM L-glutamine, 1% MEM nonessential amino acids, 1% Origen, 25 mg/ml gentamicin, 100 mM hypoxanthine, 0.4 mM aminopterin, and 16 mM thymidine). The cells were allowed to sit for 4 hours at 370 C, an additional 360 mL of 370 C Fusion Medium was added to the flask, the flask was swirled to resuspend the cells. The cells were then seeded at 200 mL/well in thirty 96-well flat bottom tissue culture plates (Costar, 3595) per fusion. The fusion plates were placed in a humidified 370 C incubator at 5% $CO_2$ for 7-10 days. The media was changed by taking off 100 ml medium adding 100 ml HT medium after 7 days.

Detection of Rat Anti-Murine MCP-1 IgG Antibodies in Rat Serum

Solid phase EIA was used to screen rat sera for antibodies specific for rMuMCP-1. Briefly, plates (Costar, 9018) were coated with rMuMCP-1 at 1 µg/mL in PBS, pH 7.4 on to 96-well EIA plates (Nunc) and incubated overnight at 4° C. The plates were then washed three times in 0.15 M saline with 0.02% v/v Tween 20, the wells were then blocked with 1% (w/v) BSA (Sigma) in PBS, 200 µL/well for 1 hour at 37° C. Plates were used immediately or frozen at −20° C. for future use. The diluted sera were incubated on the rMuMCP-1 coated plates at 50 µL/well at 37° C. for 0.5 hour. The plates were washed and then probed with 50 µL/well HRP-labeled goat anti-Rat IgG (Fc) specific antibody (Jackson Immune Research Cat#112-035-071) diluted 1:20,000 in 1% BSA-PBS for 30 minutes at 37° C. The plates were again washed and 100 µL/well of citrate-phosphate substrate solution (0.1M citric acid, 0.2M sodium phosphate, 0.01% $H_2O_2$, 1 mg/mL OPD (Sigma) was added for approximately 15 minutes at RT. The reaction was stopped by the addition of 25 µL/well, 4N $H_2SO_4$. The absorbance was measured at 490 nm by an automated plate spectrophotometer.

Detection of Rat IgG Anti-Murine MCP-1 Antibodies in Hybridoma Supernatant

Hybridomas arising from the fusion of rat lymphocytes with murine myeloma cells were evaluated by EIA for their ability to secrete anti-MuMCP-1 antibodies. Plates were coated with rMuMCP-1 at 1 µg/mL in PBS overnight at 4° C., washed and blocked as above. Undiluted hybridoma supernatants were incubated on plates for 30 minutes at RT. The detection antibody was HRP-labeled goat anti-Rat IgG Fc specific antibody diluted 1:20,000 in 1% BSA-PBS for 30 minutes at 37° C. Cells in positive wells were transferred to 24-well plates to increase cell numbers and later subcloned by limiting dilution. Isotype determination of the antibodies was accomplished by use of Rat MonoAB ID/SP kit (Zymed Cat#93-9550) in EIA format.

Five positive clones were tested for the ability to neutralize the capability of murine MCP-1 to promote chemotaxis of THP-1 cells as described in EXAMPLE 5. The best clone of the five was selected on that basis (C751).

A total of 5 antibodies specific for murine MCP-1 were identified via EIA were resulted from the two fisions (Table 4).

TABLE 4

| Fusion Name | Fusion Partner | C Code | Isotype | Conc.-dep. inhibiton of Chemotaxis |
|---|---|---|---|---|
| RMMCP-1 | FO (PEG$_{1450}$) | C588 | IgG2aκ | Yes |
|  |  | C750 | IgG2aκ | Yes |
|  |  | C751 | IgG2aκ | Yes |
| MuMCP-1 | FO (PEG$_{3000}$) | C592 | IgG2aκ | No |
|  |  | C590 | IgG1κ | No |

Neutralization Capacity of Rat Anti-Murine MCP-1 Antibodies

The rat anti-murine MCP-1 Mabs were assayed for their ability to inhibit the chemotactic effect of murine MCP-1 on THP-1 murine monocyte cells. All three Mabs from the first fusion: C588, C750 and C751, demonstrated moderate inhibition of murine MCP-1 induced chemotaxis as compared with a commercial positive control antibody. However, the remaining two Mabs did not inhibit chemotaxis and in fact appear to enhance the chemotactic properties of murine MCP-1.

EXAMPLE 6

In Vivo Angiogenesis

Angiogenesis is a complex process involving fibroblast or other pluripotent stem cell migration and differentiation. The ultimate goal of the process is to supply metabolically active or growing tissues with oxygen and nutrients, thus, a new blood supply. Angiogenesis is therefore measured in formally avascular tissue as the increse in hemoglobin. Angiogenesis can be induced in artificially implanted basement membrane, Matrigel. Matrigel is a solubilized basement membrane preparation extracted from the Engel-Holm-Swarm (EHS) mouse sarcoma, a tumor rich in extracellular matrix proteins. The major component is laminin, but Matrigel also contains trace amounts of fibroblast growth factor, TGF-beta, tissue plasminogen activator, and other growth factors that occur naturally in the EHS tumor. Matrigel is the basis for several types of tumor cell invasion assays and provides the necessary substrate for the study of angiogenesis. Matrigel forms a soft gel plug when injected subcutaneously into mice and supports an intense vascular response when supplemented with angiogenic factors.

The present model relies on human tumor cells imiplanted in Matrigel, in vivo, to supply the necessary stimuli for host angiogenesis. In this case, the host is an immunocompromised mouse. The host treatments therefore, simulate systemic therapy of a patient with either primary or metastatic neoplastic disease.

Animal and Study Design

Forty-two nude female mice (4-6 weeks old) obtained from Charles River (Raleigh, N.C.) were group housed (6/cage) in filter topped plastic cages and supplied, ad libitum, with autoclaved food and water. Matrigel prepared from the Engelbreth-Holm-Swam (EHS) tumor was obtained from Becton Dickinson (Lot # 005032, Bedford, Mass.).

Human breast cancer cells, MDA-MB 231M and MDA-MB 435S, human pancreatic cancer cells PANC-1 were cultured in DMEM medium containing 10% FBS. Cells were negative for mycoplasma, viral and bacterial contamination. Cells were replated 72 hrs before the start of the study. On the day of the study, cells were trypsinized to generate single cell suspensions in serum free DMEM. An aliquot was used for cell counting by hemocytometer.

Frozen Matrigel was thawed overnight at 4° C. Liquid Matrigel was maintained at 4° C. Keeping test tubes, syringes and pipets on ice, Matrigel was kept on ice inside the tissue culture hood. Tumor cell suspension (5 million cells/ml or 20 million cells/ml) was prepared in serum free DMEM and were kept on ice. Matrigel-tumor cell suspension was prepared by mixing 9 ml of Matrigel solution with 1 ml of tumor cells containing 5 million cells or 20 million cells. Tumor cell-Matrigel suspension was well mixed and was incubated at 4° C. for 5 min before implantation into mice. The final concentrations was 0.5 million cells/ml in 10 mg/ml of Matrigel or 2 million cells/ml in 10 mg/ml of Matrigel.

On day 1 of the study, 42 nude mice were randomized into 7 groups (n=6/group). Animals were anesthetized with Ketamine (90 mg/kg, i.p.) and weighed. The mice were injected in two sites with 0.5 ml of Matrigel and cell type and number as detailed in Table 5). Cold syringes were used in order to avoid solidification of Matrigel before the injection. The injection sites were located on the dorsal side of the approximately 0.5 inches caudal to the last rib and 0.5 inches from the backbone on each side.

TABLE 5

| Group Number | Animals/ Group | Matrigel (M) contents | Number of Cells per plug (×10$^6$) |
|---|---|---|---|
| 1 | 6 | M + DMEM | |
| 2 | 6 | M + MDA-MB 231 M | 0.25 |
| 3 | 6 | M + MDA-MB 231 M | 1.0 |
| 4 | 6 | M + MDA-MB 435 S | 0.25 |
| 5 | 6 | M + MDA-MB 435 S | 1.0 |
| 6 | 6 | M + PANC1 | 0.25 |
| 7 | 6 | M + PANC1 | 1.0 |

On day 9, all mice were euthanized by $CO_2$ asphyxiation. Plugs were surgically removed and carefully transferred to 24 well cell culture plates at room temperature. Images of plugs were recorded using a digital camera and processed using Adobe Photoshop progra. The plugs were weighed, minced and incubated in 1 ml Drabkin's solution (Sigma, St. Louis, Mo.) in individual 24-well plates. The plates were kept at 4° C. in a rocking shaker for 2-3 days to allow for complete breakdown of plugs and red blood cells, and the release of hemoglobin. Hemoglobin was measure spectrophotometrically. The content determined using a standard curve and expressed as milligrams of hemoglobin per gram of Matrigel. Means±SEM were calculated using the Student's two tailed unpaired t test; $p<0.05$ was considered statistically significant.

Results

Plugs in the Matrigel alone control group (Group 1) were semi-transparent with no visible angiogenesis response. Angiogenesis response was evident in plugs containing MDA-MB 231M cells (Groups 2 and 3) by the presence of blood in these plugs. More extensive vascularization was observed in plugs containing MDA-MB 435S and PANC-1 cells. In addition, the degree of angiogenesis response was proportional to the number of tumor cells imbedded in the plug. The angiogenesis stimulating activity of these three tumor cell lines are MDA-MB 231M<MDA-MB 435S<PANC-1.

The extent of vascularization in Matrigel plugs was determined by hemoglobin content in these plugs using Drabkin Kit. Hemoglobin content was expressed in mg Hb/gm Matrigel (Table 6). The degree of angiogenesis response measured by hemoglobin correlates well to that reflected by the macroscopic appearance of these plugs. Plugs with 1 million cells/plug, PANC-1 and MDA-MB 435S cells stimulated significantly higher levels of angiogenesis response as compared to MDA-MB231M or Matrigel alone ($p<0.001$, FIG. 2). Interestingly, the capacity of these tumor cells in inducing angiogenesis followed the rank level of MCP-1 production in culture supernate by these cells, PANC-1, MDA-MB 435S and MDA-MB 231M were 60,000, 5700 and 26 pg/ml/10E6 cells, respectively.

TABLE 6

| | Matrigel alone | MDA-MB 231M* | MDA-MB 231M** | MDA-MB 435S* | MDA-MB 435S** | PANC-1* | PANC-1** |
|---|---|---|---|---|---|---|---|
| 1 | 2.22 | 5.59 | 7.24 | 3.97 | 3.39 | 4.82 | 12.96 |
| 2 | 1.11 | 2.35 | 2.97 | 4.19 | 6.68 | 4.51 | 9.09 |
| 3 | 1.15 | 2.93 | 2.24 | 3.63 | 3.56 | 4.71 | 13.58 |
| 4 | 1.41 | 1.79 | 4.00 | 3.86 | 7.42 | 6.21 | 10.90 |
| 5 | 1.32 | 5.75 | 1.97 | 7.05 | 6.87 | 5.48 | 9.22 |
| 6 | 2.15 | 2.90 | 4.96 | 8.66 | 6.97 | 5.39 | 12.26 |
| 7 | 1.58 | 2.41 | 2.18 | 3.82 | 7.44 | 5.67 | 14.15 |
| 8 | 2.58 | 2.48 | 2.67 | 6.86 | 7.60 | 4.46 | 10.26 |
| 9 | 0.92 | 3.50 | 5.26 | 3.07 | 14.13 | 7.64 | 12.12 |
| 10 | 1.33 | 5.69 | 5.07 | 7.34 | 8.08 | 5.46 | N/A |
| 11 | 1.26 | 2.70 | 7.86 | 5.58 | 6.84 | 6.73 | 18.34 |
| 12 | 1.36 | 4.09 | 6.35 | 9.09 | 9.02 | N/A | 7.00 |
| Hb (mean) | 1.53 | 3.51 | 4.40 | 5.59 | 7.33 | 5.55 | 11.81 |
| STD | 0.51 | 1.43 | 2.05 | 2.12 | 2.71 | 0.99 | 3.06 |

A two tailed, unpaired t test was used. $P<0.001$ compared to Matrigel alone; for all other groups and both cell numbers. $P<0.001$ for MDA-MB435S and PANC-1 at 1 million cells compared to MDA-MB231M at 1.0 million cells/plug.

The study described here demonstrated a simple assay to measure in vivo angiogenesis response induced by tumor cells imbedded in Matrigel in nude mice. The degree of angiogenesis is dependent on the number of tumor cells imbedded in the plug and the MCP-1 secreting capacity of the cell line. Among the three tumor cells lines tested, pancreatic cancer (PANC-1) and breast cancer (MDA-MB 435S) are more potent in stimulating angiogenesis compared to breast cancer (MDA-MB 231M) cells as determined by hemoglobin content and secrete 200 or 2000-fold more MCP-1 than MB 231 cells.

EXAMPLE 7

In Vivo Inhibiton of Human Tumor Driven Angiogenesis by Anti-MCP1 Antibody

The protocol established in EXAMPLE 6 was used except that 5 million tumor cells were added to 10 ml of matrigel giving a final concentration of $0.5 \times 10^6$ tumor cells per ml Matrigel. Only MDA MB 435S and PANC-1 tumor cells were used.

Mouse anti-human MCP-1 antibody (C775), 1.48 EU/mg protein), stock concentration 2 mg/ml, and rat anti-mouse JE antibody (C751, 1.6 EU/mg protein), stock concentration 2 mg/ml were used in this study. Both antibodies were tested for their ability to block MCP-1 mediated chemotaxis assay. Antibodies were administered i.p. on day 1 and day 5 as defined in Table 7.

Anti-MCP-1 antibody (C775) alone or in combination with anti-JE antibody (C751), was injected i.p., at 50 mg/kg as defined in Table 7, at day 1 (before Matrigel injection i.e., immediately after anesthesia) and day 5. The antibodies were diluted to 2 mg/ml and administered at 0.5 ml per 20 grams of body weight i.p. The injections of each mAb were separated by 30 minutes for each treatment regimen.

TABLE 7

| Group Number | Animals/Group | Matrigel (M) contents | Treatment |
|---|---|---|---|
| 1 | 6 | M + DMEM | PBS |
| 2 | 6 | M + PANC-1 | PBS |
| 3 | 6 | M + PANC-1 | Anti-MCP-1 + PBS |
| 4 | 6 | M + PANC-1 | Anti-MCP-1 + Anti-JE |
| 5 | 6 | M + MDA-MB 435 S | PBS |
| 6 | 6 | M + MDA-MB 435 S | Anti-MCP-1 + PBS |
| 7 | 6 | M + MDA-MB 435 S | Anti-MCP-1 + Anti-JE |

On day 9, all mice were euthanized by CO2 asphyxiation. Matrigel plugs were surgically removed and carefully transferred to 24-well cell culture plates at room temperature. Gross images of plugs were recorded using digital camera attached to either a Phase 3 microscope or a dissecting microscope (NIKON SMZ 1500) for computerized imaging of selected plugs harvested from the animals received different treatments. After photographic analysis, plugs were weighed, minced and incubated in Drabkin's solution at 4° C. for 7 days to determine hemoglobin content, which is used as an indirect index of the angiogenic response. There were 12 plugs in each group with a total of 82 plugs in 7 groups. Two plugs from 1 mouse in Group 2 were missing.

Results

As before, plugs in the Matrigel alone control group (Group 1) were semi-transparent with no visible angiogenic response. Significant angiogenesis occurred in plugs containing human pancreatic cancer cells PANC-1 or human breast cancer cells MDA MB 435S with a more vigorous angiogenic response produced by PANC-1 than MB 435S cells. When viewed at higher magnification, plugs with cancer cells from untreated mice developed to small tumor nodules. Systemic treatment with anti-human MCP-1 mAb at 50 mg/kg on day 1 and day 5, plus or minus anti-JE MAB, significantly inhibited both MB 435S and PANC-1 tumor cell-induced angiogenesis, as reflected by the semitransparent appearance of these plugs and at the same time appeared to completely inhibit tumor formation.

Figure 3:
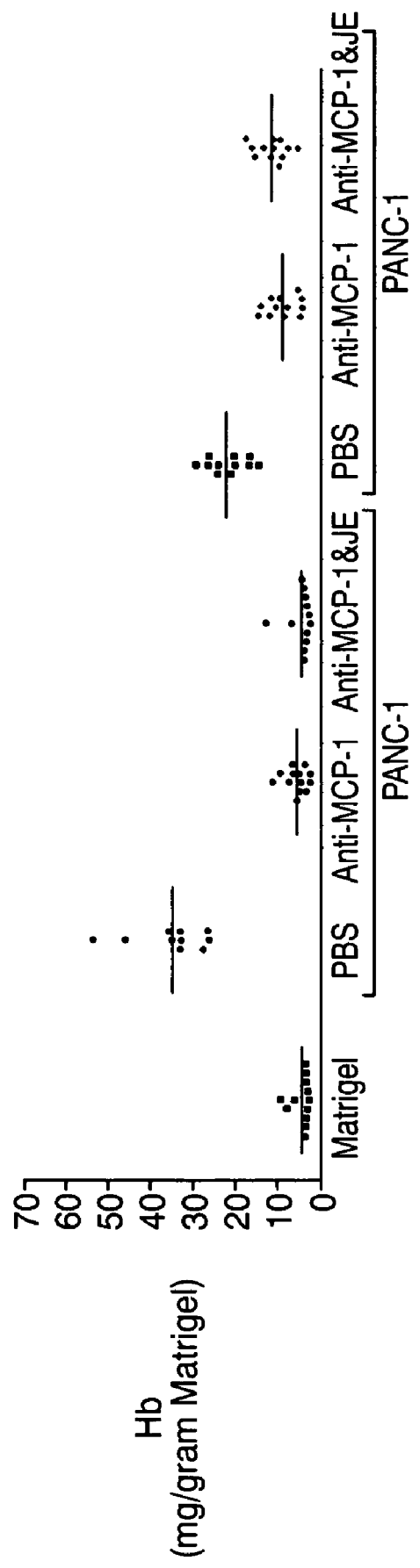
FIG. 3 shows a frequency plot for hemoglobin measurement data from individual Matrigel plugs from mice receiving no treatment or various anti-MCP-1 antibodies systemically.

The results of the hemoglobin assays are shown in FIG. 3. One-way analysis of variance (ANOVA) with the Bonferroni test was performed for multiple comparisons. All anti-MCP-1 treated groups had significantly less hemoglobin at P<0.001 then the PBS treated animals for the PANC-1 or MDA-MB435S groups.

Tumor growth of PANC-1 human pancreatic cancer cells or MDA MB 435S human breast cancer cells in Matrigel plugs appeared to be completely inhibited by systemic treatment with mouse anti-human MCP-1 antibodies, or in combination with rat anti-mouse JE antibodies in the 9-day study period. It was not possible to distinguish what contribution the anti-JE Mab may have made to the tumor cell angiogenic activity or to tumor cell proliferation.

EXAMPLE 8

Dose Finding in the Angiogenesis Model for Anti-MCP-1 Antibody

In this experiment, we evaluated the minimum biologically active dose required for anti-MCP-1 mAb, anti-JE, a monoclonal antibody to the murine homolog of MCP-1, and a chimeric anti-JE to inhibit pancreatic cancer cell-induced angiogenesis.

Materials and Methods

The mice, PANC-1 cell line, and cells concentration per gm Matrigel ($0.5 \times 10^6$) were as described in Example 7. Mouse anti-human MCP-1 antibody (C775), 1.48 EU/mg protein), stock concentration 2 mg/ml, and rat anti-mouse JE antibody (C751, 1.6 EU/mg protein), stock concentration 2 mg/ml were used in this study. Chimeric (human/mouse) Anti-JE (C1053B) namely, PHD001, having 1.0 EU/mg protein was also generated at Centocor. PHD001 is a phage-derived antibody. In the chimeric format, the Fab portion ($2/3$ of the molecule) is human (screened from a human mAb library), and the Fc portion ($1/3$ of the molecule) is murine. Control antibodies, mouse IgG1 (Clone15H6, Cat # 0102-14), and rat IgG2a (Clone KLH/G2a-1-1, Cat # 0117-14) obtained from Southern Biotechnology Associates, Inc., Birmingham, Ala. 35226 with a stock concentrations of 0.5 mg/ml were used in this study. Antibodies, C775, C751, and PHD001, and control antibodies, mouse IgG1, and rat IgG2a were administered I.P. on day 1 and day 5 according to the Table 8.

TABLE 8

| Group | Animals per Group | Treatment | Antibody Dose (mg/kg body weight) |
|---|---|---|---|
| 1 | 6 | PBS | N/A |
| 2 | 6 | PBS | N/A |
| 3 | 6 | Anti-MCP-1 (C775) | 0.1 mg/kg |
| 4 | 6 | Anti-MCP-1 (C775) | 1 mg/kg |
| 5 | 6 | Anti-MCP-1 (C775) | 10 mg/kg |
| 6 | 6 | Mouse IgG1 | 10 mg/kg |
| 7 | 6 | Anti-JE (C751) | 0.1 mg/kg |
| 8 | 6 | Anti-JE (C751) | 1 mg/kg |
| 9 | 6 | Anti-JE (C751) | 10 mg/kg |
| 10 | 6 | Rat IgG2a | 10 mg/kg |
| 11 | 6 | Chimeric Anti-JE (PHD001) | 10 mg/kg |

Animals were euthanized on Day 9 as before and all plugs were photographed and processed for hemoglobin analysis as described in Examples 8 and 9.

Small tumor nodules with extensive angiogenesis have developed from PANC-1 cells embedded in Matrigel plugs. By visual, microscopic, and photographic analysis; treatment with anti-human MCP-1 mAb (C775) at 1, and 10 mg/kg on day 1 and day 5 effectively eliminated angiogenesis and at the same time appeared to completely inhibit tumor formation. Plugs from mice treated with 0.1 mg/kg (C775 had reddish color but less so than the untreated control plugs.

Similarly, systemic treatment with anti-mouse JE mAb (C751) at 1, and 10 mg/kg on day 1 and day 5 prevented PANC-1 tumor cell-induced angiogenesis, as reflected by the lack of blood vessels in these plugs. Anti-mouse JE mAb at 0.1 mg/kg reduced but did not eliminate angiogenic activity. The control rat IgG at 10 mg/kg did not inhibit PANC-1 tumor cell-induced angiogenesis. Small tumor nodules with extensive angiogenesis have developed from PANC-1 cells embedded in Matrigel plugs. Treatment with anti-mouse JE mAb at 1, and 10 mg/kg on day 1 and day 5 appeareds to completely inhibit tumor formation.

The chimeric human-mouse anti-murine JE (murine MCP-1 homolog), PHD001, used only at 10 mg/kg also completely eliminated visible and microscope evidence of angiogenesis in the plugs.

Figure 4:
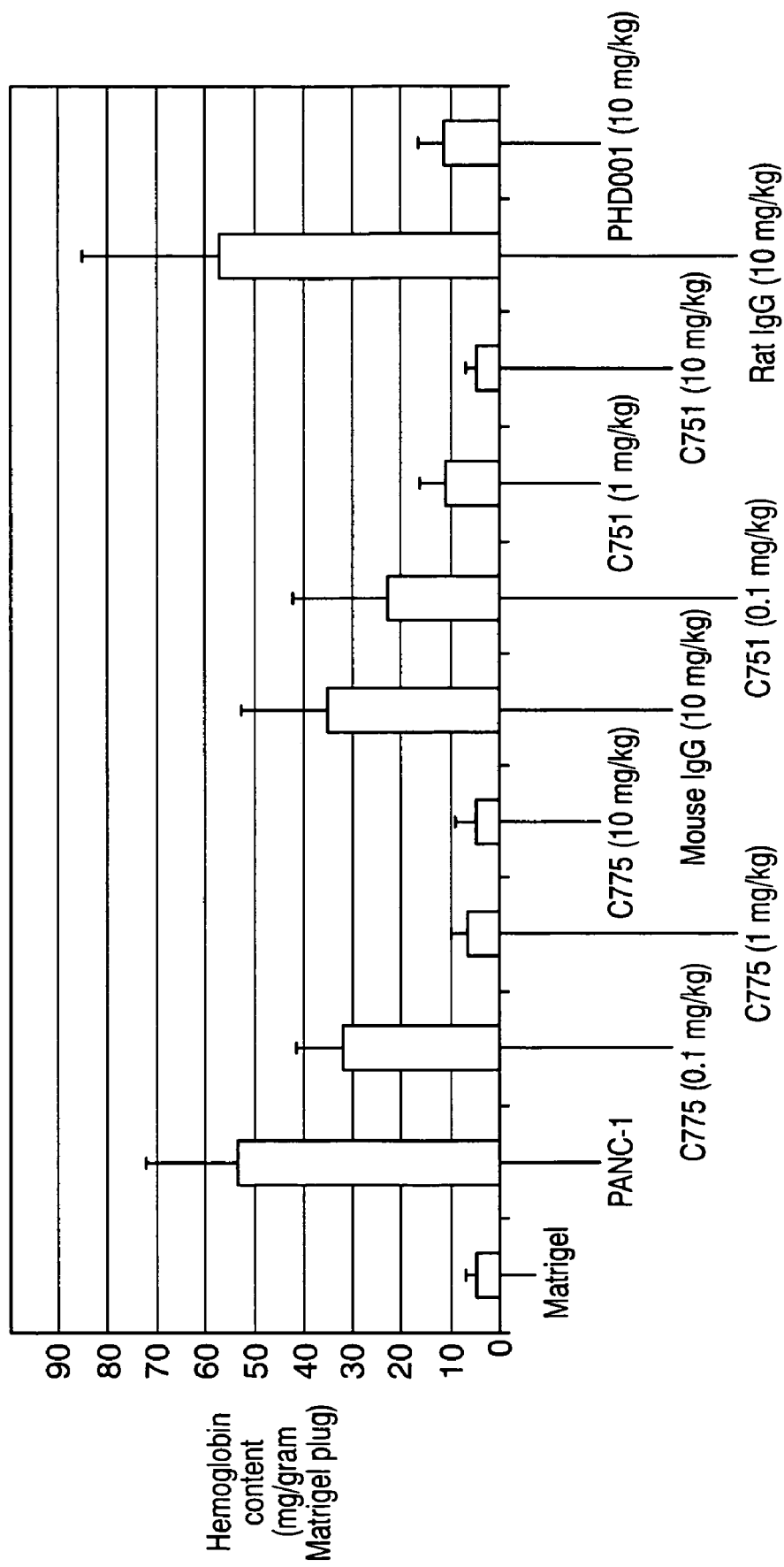
FIG. 4 shows a bar graph expressing the mean and standard deviation of hemoglobin values measured in Matrigel plugs nine days after their implantation in mice, some having received systemic treatment with anti-MCP-1 antibodies as indicated.

The visible results are confirmed by the hemoglobin assay results (FIG. 4). P value was determined by one-way analysis of variance (ANOVA) with the Bonferroni test for multiple comparisons. The results are shown in Table 9.

TABLE 9

| Group/Treatment | Hb (Mean) | SD | Statistic |
|---|---|---|---|
| Matrigel | 4.70 | 2.57 | |
| PANC-1 (PBS) | 53.47 | 18.58 | Reference |
| C775 (0.1 mg/kg) | 32.10 | 9.24 | NS |
| C775 (1 mg/kg) | 6.74 | 3.18 | P < 0.001 |
| C775 (10 mg/kg) | 5.23 | 3.91 | P < 0.0001 |
| Mouse IgG (10 mg/kg) | 35.47 | 17.52 | NS |
| C751 (0.1 mg/kg) | 23.45 | 18.56 | NS |
| C751 (1 mg/kg) | 11.45 | 4.93 | P < 0.001 |
| C751 (10 mg/kg) | 4.81 | 2.74 | P < 0.0001 |
| Rat IgG (10 mg/kg) | 57.60 | 27.65 | NS |
| PHD001 (10 mg/kg) | 11.53 | 5.58 | P < 0.001 |

NS = no significant difference

Thus, the minimal dose to effectively eliminate angiogenesis induced by PANC-1 cells was found to be between 0.1 and 1 mg/kg when given on Day 1 (day of tumor cell implantation) and Day 5 for the murine anti-human MCP-1 (C775) as well as for rat anti-murine JE (MCP-1 homolog). For a chimeric antibody with human variable regions to murine JE, the dose required is 10 mg/kg or less.

References

1. Sanders, S K. et al. Functional Differences Between Monocyte Chemotactic Protein-1 Receptor A and Monocyte Chemotactic Protein-1 Receptor B Expressed in a Jurkat T Cell. *Journal of Immunology*, 165: 4877-4883. 2000
2. Saji, H., Koike, M., Yamori, T., Saji, S., Seiki, M., Matsushima, K., and Toi, M. Significant correlation of monocyte chemoattractant protein-1 expression with neovascularization and progression of breast carcinoma. Cancer, 92: 1085-1091, 2001.
3. Ueno, T., Toi, M., Saji, H., Muta, M., Bando, H., Kuroi, K., Koike, M., Inadera, H., and Matsushima, K. Significance of macrophage chemoattractant protein-1 in macrophage recruitment, angiogenesis, and survival in human breast cancer. Clin Cancer Res, 6: 3282-3289, 2000.
4. Liss, C., Fekete, M. J., Hasina, R., Lam, C. D., and Lingen, M. W. Paracrine angiogenic loop between head-and-neck squamous-cell carcinomas and macrophages. Int J Cancer, 93: 781-785, 2001.
5. Ohta, M., Kitadai, Y., Tanaka, S., Yoshihara, M., Yasui, W., Mukaida, N., Haruma, K., and Chayama, K. Monocyte chemoattractant protein-1 expression correlates with macrophage infiltration and tumor vascularity in human esophageal squamous cell carcinomas. Int J Cancer, 102: 220-224, 2002.
6. Ohta, M., Kitadai, Y., Tanaka, S., Yoshihara, M., Yasui, W., Mukaida, N., Haruma, K., and Chayama, K. Monocyte chemoattractant protein-1 expression correlates with macrophage infiltration and tumor vascularity in human gastric carcinomas. Int J Oncol, 22: 773-778, 2003.
7. Isik, F. F., Rand, R. P., Gruss, J. S., Benjamin, D., and Alpers, C. E. Monocyte chemoattractant protein-1 mRNA expression in hemangiomas and vascular malformations. J Surg Res, 61: 71-76, 1996.
8. Taylor, L. D., C. E. Carmack, D. Huszar, K. M. Higgins, R. Mashayekh, G. Sequar, S. R. Schramm, C-C. Kuo, S. L. O'Donnell, R. M. Kay, C. S. Woodhouse, and N. Lonberg. 1993. Human immunoglobulin transgenes undergo rearrangement, somatic mutation and class switching in mice that lack endogenous IgM. International Immunology 6:579-591.
9. Lonberg, N., L. D. Taylor, F. A. Harding, M. Trounstine, K. M. Higgins, S. R. Schramm, C-C. Kuo. R. Mashayekh, K. Wymore, J. G. McCabe, D. Munoz-O'Regan, S. L. O'Donnell, E. S. G. Lapachet, T. Bengoechea, D. M. Fishwild, C. E. Carmack, R. M. Kay, and D. Huszar. 1994. Antigen-specific human antibodies from mice comprising four distinct genetic modifications. Nature 368:856-859.
10. Neuberger, M. 1996. Generating high-avidity human Mabs in mice. Nature Biotechnology 14:826.
11. Fishwild, D. M., S. L. O'Donnell, T. Bengoechea, D. V. Hudson, F. Harding, S. L. Bernhard, D. Jones, R. M. Kay, K. M. Higgins, S. R. Schramm, and N. Lonberg. 1996. High-avidity human IgG monoclonal antibodies from a novel strain of minilocus transgenic mice. Nature Biotechnology 14:845-851.
11. Wang G. et al. Homocysteine stimulates the expression of monocyte chemoattractant protein-1 receptor (CCR2) in human monocytes: possible involvement of oxygen free radicals. *Biochem J,* 357(Pt. 1): 233-40. 2001.
12. Looney J E, et al. (1992) High-level expression and characterization of a mouse-human chimeric CD4 antibody with therapeutic potential. Hum Antibodies Hybridomas 3(4): 191.
13. Scallon B J, et al. (1995) Functional comparisons of different tumour necrosis factor receptor/IgG fusion proteins. Cytokine 7(8):759.

It will be clear that the invention can be practiced otherwise than as particularly described in the foregoing description and examples.

Numerous modifications and variations of the present invention are possible in light of the above teachings and, therefore, are within the scope of the appended claims.

What is claimed is:

1. An isolated monoclonal anti-human monocyte chemoattractant protein 1 (MCP-1) antibody comprising a heavy chain variable region of SEQ ID NO:7, wherein said antibody inhibits the ability of human MCP-1 to cause positive chemotactic migration to monocytic cells.

2. The isolated monoclonal anti-MCP-1 antibody of claim 1, wherein the heavy chain variable region CDR1, CDR2 and CDR3 sequences are SEQ ID NOS: 1, 2, and 3, respectively.

3. The isolated monoclonal anti-MCP-1 antibody of claim 1, further comprising a light chain variable region comprising light chain CDRs 1-3 of SEQ ID NOS: 4-6, respectively.

4. The isolated monoclonal anti-MCP-1 antibody of claim 1, comprising human heavy chain and human light chain framework regions comprising the amino acid sequences of the heavy and light chain CDRs shown in SEQ ID NOS: 1-6.

5. The isolated monoclonal anti-MCP-1 antibody of claim 1, comprising both heavy chain and light chain variable regions comprising SEQ ID NOS: 7 and 8.

6. The isolated monoclonal anti-MCP-1 antibody of claim 1, which binds to human MCP-1 with a $K_D$ of $10^{-8}$ M or less.

7. The isolated monoclonal anti-MCP-1 antibody of claim 6, wherein said antibody binds to human MCP-1 with a $K_D$ of $10^{-9}$ M or less.

8. The isolated monoclonal anti-MCP-1 antibody of claim 6, wherein the antibody inhibits the ability of human MCP-1 to cause internal Ca2+ mobilization in THP-1 cells.

9. The isolated monoclonal anti-MCP-1 antibody of claim 1, comprising a human IgG heavy chain constant region and a human kappa light chain constant region.

10. The isolated monoclonal anti-MCP-1 antibody of claim 1, comprising an IgG1 or IgG4 heavy chain constant region.

11. A pharmaceutical composition comprising The isolated monoclonal anti-MCP-1 of claim 1 and a pharmaceutically acceptable carrier.

* * * * *